(12) United States Patent
Ragnarsdottir et al.

(10) Patent No.: US 7,431,737 B2
(45) Date of Patent: Oct. 7, 2008

(54) SYSTEM AND METHOD FOR MOTION-CONTROLLED FOOT UNIT

(75) Inventors: Heidrun G. Ragnarsdottir, Reykjavik (IS); Arinbjorn V. Clausen, Reykjavik (IS); Hjordis Thorhallsdottir, Reykjavik (IS); Helgi Jonsson, Reykjavik (IS)

(73) Assignee: Össur hf., Reykjavik (IS)

( * ) Notice: Subject to any disclaimer, the term of this patent is extended or adjusted under 35 U.S.C. 154(b) by 0 days.

(21) Appl. No.: 11/057,391

(22) Filed: Feb. 11, 2005

(65) Prior Publication Data
US 2005/0192677 A1    Sep. 1, 2005

Related U.S. Application Data

(60) Provisional application No. 60/544,259, filed on Feb. 12, 2004, provisional application No. 60/588,232, filed on Jul. 15, 2004.

(51) Int. Cl.
*A61F 2/24* (2006.01)
*A61F 2/66* (2006.01)
(52) U.S. Cl. .............................. 623/24; 623/47; 623/50
(58) Field of Classification Search .................. 623/24, 623/26, 47–50; 901/9–11
See application file for complete search history.

(56) References Cited

U.S. PATENT DOCUMENTS

| | | | |
|---|---|---|---|
| 3,820,168 A | 6/1974 | Horvath | |
| 3,995,324 A | 12/1976 | Burch | |
| 4,030,141 A | 6/1977 | Graupe | |
| 4,065,815 A | 1/1978 | Sen-Jung | |
| 4,094,086 A | 6/1978 | Gevers | |
| 4,179,759 A | 12/1979 | Smith | |
| 4,209,860 A | 7/1980 | Graupe | |
| 4,212,087 A | 7/1980 | Mortensen | |
| 4,387,472 A | 6/1983 | Wilson | |

(Continued)

FOREIGN PATENT DOCUMENTS

DE    4229330    3/1994

(Continued)

OTHER PUBLICATIONS

PCT International Search Report and Written Opinion mailed Aug. 19, 2005, Appl. No. PCT/US2005/004878, 15 pages.

(Continued)

*Primary Examiner*—Bruce E. Snow
(74) *Attorney, Agent, or Firm*—Knobbe Martens Olson & Bear LLP

(57) ABSTRACT

A system and method associated with the movement of a limb. In one example, the system, such as a prosthetic or orthotic system, includes an actuator that actively controls, or adjusts, the angle between a foot unit and a lower limb member. A processing module may control movement of the actuator based on data obtained from a sensor module. For instance, sensing module data may include information relating to the gait of a user and may be used to adjust the foot unit to substantially mimic the movement of a natural, healthy ankle. The system may further accommodate, for example, level ground walking, traveling up/down stairs, traveling up/down sloped surfaces, and various other user movements. In addition, the processing module may receive user input or display output signals through an external interface. For example, the processing module may receive a heel height input from the user.

43 Claims, 11 Drawing Sheets

U.S. PATENT DOCUMENTS

| | | | |
|---|---|---|---|
| 4,521,924 A | 6/1985 | Jacobsen et al. |
| 4,558,704 A | 12/1985 | Petrofsky |
| 4,569,352 A | 2/1986 | Petrofsky et al. |
| 4,711,242 A | 12/1987 | Petrofsky |
| 4,776,852 A | 10/1988 | Rubic |
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards |
| 5,044,360 A | 9/1991 | Janke |
| 5,062,856 A | 11/1991 | Sawamura et al. |
| 5,062,857 A | 11/1991 | Berringer |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,181,931 A | 1/1993 | Van de Veen |
| 5,201,772 A | 4/1993 | Maxwell |
| 5,217,500 A | 6/1993 | Phillips |
| 5,252,102 A | 10/1993 | Singer et al. |
| 5,336,269 A | 8/1994 | Smits |
| 5,376,133 A | 12/1994 | Gramnas |
| 5,376,137 A | 12/1994 | Shorter et al. |
| 5,383,939 A | 1/1995 | James |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,504,415 A | 4/1996 | Podrazhansky et al. |
| 5,545,232 A | 8/1996 | Van de Veen |
| 5,545,233 A | 8/1996 | Fitzlaff |
| 5,571,205 A | 11/1996 | James |
| 5,571,212 A | 11/1996 | Cornelius |
| 5,571,213 A | 11/1996 | Allen |
| 5,586,557 A | 12/1996 | Nelson et al. |
| 5,650,704 A | 7/1997 | Pratt et al. |
| 5,656,915 A | 8/1997 | Eaves |
| 5,662,693 A | 9/1997 | Johnson et al. |
| 5,704,945 A | 1/1998 | Wagner et al. |
| 5,704,946 A | 1/1998 | Greene |
| 5,728,170 A | 3/1998 | Becker et al. |
| 5,746,774 A | 5/1998 | Kramer et al. |
| 5,779,735 A | 7/1998 | Molino |
| 5,800,568 A | 9/1998 | Atkinson et al. |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Conner |
| 5,919,149 A | 7/1999 | Allum |
| 5,955,667 A | 9/1999 | Fyfe |
| 5,957,981 A | 9/1999 | Gramnas |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| 6,061,577 A | 5/2000 | Andrieu et al. |
| 6,091,977 A | 7/2000 | Tarjan et al. |
| 6,113,642 A | 9/2000 | Petrofsky et al. |
| 6,129,766 A | 10/2000 | Johnson et al. |
| 6,165,226 A | 12/2000 | Wagner |
| 6,183,425 B1 | 2/2001 | Whalen et al. |
| 6,187,051 B1 | 2/2001 | van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,361,570 B1 | 3/2002 | Gow |
| 6,373,152 B1 | 4/2002 | Wang et al. |
| 6,409,695 B1 | 6/2002 | Connelly |
| 6,423,098 B1 | 7/2002 | Biedermann |
| 6,425,925 B1 | 7/2002 | Grundel |
| 6,430,843 B1 | 8/2002 | Potter et al. |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,602,295 B1 | 8/2003 | Doddroe et al. |
| 6,610,101 B2 | 8/2003 | Herr et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,719,806 B1 | 4/2004 | Zahedi et al. |
| 6,740,123 B2 | 5/2004 | Davalli et al. |
| 6,755,870 B1 | 6/2004 | Biedermann et al. |
| 6,764,520 B2 | 7/2004 | Deffenbaugh et al. |
| 6,770,045 B2 | 8/2004 | Naft et al. |
| 6,876,135 B2 | 4/2005 | Pelrine et al. |
| 6,955,692 B2 | 10/2005 | Grundei |
| 7,029,500 B2 | 4/2006 | Martin |
| 7,063,727 B2 | 6/2006 | Van Phillips et al. |
| 7,131,998 B2 | 11/2006 | Pasolini |
| 7,137,998 B2 | 11/2006 | Bedard et al. |
| 7,147,667 B2 | 12/2006 | Bedard |
| 7,164,967 B2 | 1/2007 | Etienne-Cummings et al. |
| 2001/0029400 A1 | 10/2001 | Deffenbaugh et al. |
| 2002/0040601 A1 | 4/2002 | Fyfe et al. |
| 2002/0052663 A1 | 5/2002 | Herr et al. |
| 2002/0087216 A1 | 7/2002 | Atkinson et al. |
| 2002/0138153 A1 | 9/2002 | Koniuk |
| 2002/0183803 A1 | 12/2002 | Fang et al. |
| 2002/0198604 A1 | 12/2002 | Schulman et al. |
| 2003/0029247 A1 | 2/2003 | Biedermann |
| 2003/0067245 A1 | 4/2003 | Pelrine et al. |
| 2003/0093158 A1 | 5/2003 | Phillips et al. |
| 2003/0120353 A1 | 6/2003 | Christensen |
| 2003/0120385 A1 | 6/2003 | Etienne-Cummings et al. |
| 2004/0049290 A1 | 3/2004 | Bedard |
| 2004/0054423 A1 | 3/2004 | Martin |
| 2004/0064195 A1 | 4/2004 | Herr |
| 2004/0088057 A1 | 5/2004 | Bedard |
| 2004/0111163 A1 | 6/2004 | Bedard et al. |
| 2004/0181289 A1 | 9/2004 | Bedard |
| 2004/0193286 A1 | 9/2004 | Grundei |
| 2004/0263127 A1 | 12/2004 | Turner |
| 2004/0267379 A1 | 12/2004 | Pasolini |
| 2005/0004495 A1 | 1/2005 | Goswami |
| 2005/0010139 A1 | 1/2005 | Aminian et al. |
| 2005/0143838 A1 | 6/2005 | Collier |
| 2005/0197717 A1 | 9/2005 | Ragnarsdottir et al. |
| 2005/0283257 A1 | 12/2005 | Bisbee et al. |
| 2006/0041321 A1 | 2/2006 | Christensen |
| 2006/0064195 A1 | 3/2006 | Kern et al. |
| 2006/0122710 A1 | 6/2006 | Bedard |
| 2006/0122711 A1 | 6/2006 | Bedard et al. |
| 2006/0136072 A1 | 6/2006 | Bisbee et al. |
| 2006/0155385 A1 | 7/2006 | Martin |

| | | | |
|---|---|---|---|
| 2007/0027555 | A1 | 2/2007 | Palmer |

FOREIGN PATENT DOCUMENTS

| | | | |
|---|---|---|---|
| DE | 195 21 464 | A1 | 6/1995 |
| DE | 197 54 690 | A | 7/1999 |
| EP | 0 549 855 | A2 | 7/1993 |
| EP | 0628296 | A2 | 12/1994 |
| EP | 0718951 | A | 6/1996 |
| EP | 1066793 | | 1/2001 |
| EP | 1 166 726 | A1 | 1/2002 |
| EP | 1340478 | | 9/2003 |
| FR | 2623086 | | 11/1987 |
| GB | 2201260 | A | 8/1988 |
| GB | 2244006 | A | 11/1991 |
| GB | 2 260 495 | A | 4/1993 |
| GB | 2301776 | | 12/1996 |
| GB | 2 302 949 | A | 2/1997 |
| GB | 2367753 | | 8/1998 |
| GB | 2328160 | A | 2/1999 |
| GB | 2334891 | A | 9/1999 |
| GB | 2338653 | A | 12/1999 |
| JP | 11056885 | | 3/1999 |
| JP | 11000345 | A2 | 6/1999 |
| JP | 20011277175 | | 10/2001 |
| JP | 2002/191654 | A | 7/2002 |
| WO | WO 93/24080 | A1 | 12/1993 |
| WO | WO 94/06374 | | 3/1994 |
| WO | WO 95/26171 | A1 | 10/1995 |
| WO | WO 96/41598 | | 12/1996 |
| WO | WO 96/41599 | A | 12/1996 |
| WO | WO 97/00661 | A1 | 1/1997 |
| WO | WO 98/2552 | | 6/1998 |
| WO | WO 98/38951 | A1 | 9/1998 |
| WO | WO 99/05991 | A2 | 2/1999 |
| WO | WO 99/08621 | A2 | 2/1999 |
| WO | 0902547 | A | 3/1999 |
| WO | WO 99/29272 | | 6/1999 |
| WO | WO 00/27318 | A | 5/2000 |
| WO | WO 00/30572 | A1 | 6/2000 |
| WO | WO 00/38599 | | 7/2000 |
| WO | WO 01/176466 | A2 | 3/2001 |
| WO | 1107420 | A | 6/2001 |
| WO | WO 01/50986 | A1 | 7/2001 |
| WO | WO 01/72245 | | 10/2001 |
| WO | WO 00/71061 | | 11/2001 |
| WO | 1 166 726 | A1 | 1/2002 |
| WO | WO 03003953 | | 1/2003 |
| WO | WO 03/088373 | A | 10/2003 |
| WO | WO 03/0896245 | A | 10/2003 |
| WO | WO 2004/017871 | | 3/2004 |
| WO | WO 2004/017872 | | 3/2004 |
| WO | WO 2004/017873 | | 3/2004 |
| WO | WO 05/041819 | 2 | 5/2005 |

OTHER PUBLICATIONS

U.S. Appl. No. 11/056,344, filed Feb. 11, 2005, Ragnarsdottir et al.
U.S. Appl. No. 60/572,996, filed May 19, 2004, Bisbee, III et al.
Copes/Bionic Ankle, The Most Significant Development in Ankle Prosthetics in Over a Half Century, 1985.
H. Dietl, H. Bargehr, Der Einsatz von Elektronik bei Prothesen zur Versorgung der unteren Extremitat, Med. Orth. Tech. 117 1997, pp. 31-35.
U.S. Appl. No. 11/367,049, filed Mar. 1, 2006.
U.S. Appl. No. 11/367,048, filed Mar. 1, 2006.
Proteor, Assembly and Adjustment Instructions for 1P50-R, pp. 1-21 Sep. 2004.
English translation of JP 2002-191654 A.
English abstract of EP 1 169 982 A1.
Townsend M A et al., "Biomechanics and modeling of bipedal climbing and descending." Journal of Biomechanics 1976, vol. 9, No. 4, pp. 227-239, XP008078405.
Suga, T., et al., "Newly designed computer controlled knee-ankle-foot orthosis (Intellegent Orthosis)", Prostetics and Orthotics International, 1998, 22, 230-239.
Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.
Flowers, et al., Journal of Biomechanicals Engineering: Transactions of the ASME; Feb. 1977, pp. 3-8.
Blumentritt, Siegmar, Ph.D., et al.; "Design Principles, Biomedical Data and Clinical Experience With A Polycentric Knee Offering Controlled Stance Phase Knee Flexion: A Preliminary Report", 1997, Journal of Prothetics and Orthotics, vol. 9, No. 1, 18-24.
Carlson et al., "Smart Prosthetics Based on Magnetorheological Fluids", 8th Annual Symposium on Smart Structures and Materials, Mar. 2001, 9 pages.
Elliott, Scott B.; "MR Microprocessor-Controlled Swing and Stance," Presentation to American Academy of Orthotists & Prosthetists (Feb. 4, 2004), 81 pages.
Herr, et al., "User-adaptive control of a magnetorheological prosthetic knee", Industrial Robot: an International Journal, vol. 30, No. 1, (2003) pp. 42-55.
"MT9 Inertial 3D Motion Tracker," Xsens Technologies B.V., available at http://www.xsens.com/download/MT9_brochure.pdf (at least as early as Oct. 2004), printed Jul. 20, 2006, 2 pages.
Otto Bock, Modular Knee Joints, http://www.healthcare.ottobock.com/technical_orthopedics/beinprothesen/sites/knee.htm, printed Jul. 10, 2002, 4 pages.
Otto, Judith, "Prosthetic Knees: What's on the Way?", The O&P edge, http://www.oandp.com/edge/issues/articles/2003-10_02.asp, Oct. 2003, 5 pages.
Otto, Judith, "Prosthetic Knees: What's Currently New and Impressive?", The O&P Edge, http://www.oandp.com/edge/issues/articles/2003-10_03.sp, Oct. 2003, 4 pages.
Van der Loos, H.F.M., et al., "ProVAR Assistive Robot System Architecture", Proceedings of the 1999 IEEE International Conference on Robotics & Automation; Detroit, Michigan, May 1999, pp. 741-46.

| Possible Transits: From State to State | Stance | Level Ground Walking | Ascending Stairs | Descending Stairs | Incline (up) | Decline | Sitting Down | Sitting | Standing Up | Adjust Heel Height |
|---|---|---|---|---|---|---|---|---|---|---|
| Stance | N/A | Toe Clearance | -10° | -10° | -2.5°, -5° | +2.5°, +5° | No Action | | | Set Heel Height |
| Level Ground Walking | No Action | N/A | -10° | -10° | -2.5°, -5° | +2.5°, +5° | | | | |
| Ascending Stairs | User Setpoint | Toe Clearance | N/A | -10° | -2.5°, -5° | +2.5°, +5° | | | | |
| Descending Stairs | User Setpoint | Toe Clearance | -10° | N/A | | +2.5°, +5° | | | | |
| Incline (up) | No Action | Toe Clearance | -10° | | N/A | | | | | |
| Decline | No Action | Toe Clearance | | -10° | -2.5°, -5° | N/A | | | | |
| Sitting Down | | | | | | | | Relax Ankle | N/A | |
| Sitting | | | | | | | N/A | | User Setpoint | N/A |
| Standing Up | User Setpoint | | | | | | User Setpoint | N/A | | Set Heel Height |
| Adjust Heel Height | User Setpoint | | | | | | User Setpoint | User Setpoint | N/A | |

FIG. 10

SYSTEM AND METHOD FOR MOTION-CONTROLLED FOOT UNIT

RELATED APPLICATIONS

The present application claims the benefit of priority under 35 U.S.C. § 119(e) of U.S. Provisional Application No. 60/544,259, filed Feb. 12, 2004, and entitled "LOWER LIMB PROSTHESIS WITH ANKLE-MOTION-CONTROLLED FOOT," and U.S. Provisional Application No. 60/588,232, filed Jul. 15, 2004, and entitled "PROSTHETIC OR ORTHOTIC SYSTEM WITH ANKLE-MOTION-CONTROLLED FOOT," each of which is incorporated herein by reference in its entirety and is to be considered a part of this specification.

BACKGROUND OF THE INVENTION

1. Field of the Invention

Preferred embodiments of this invention relate to systems and methods having a motion-controlled limb and, in particular, an ankle-motion-controlled foot.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

The number of disabled persons and amputees is increasing each year as the average age of individuals increases, as does the prevalence of debilitating diseases such as diabetes. As a result, the need for prosthetic and orthotic devices is also increasing. Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

SUMMARY OF THE INVENTION

Accordingly, one embodiment of the invention includes a prosthetic or orthotic system that is self-powered and that mimics the natural movement of a healthy limb, and in particular, the movement of a healthy ankle. Another embodiment of the invention includes a sensor system and a control system that manage the motion of the prosthetic or orthotic system so as to facilitate movement by the disabled person or amputee.

One embodiment of the invention includes a system associated with the movement of a limb. In one embodiment, the system comprises a foot unit; an attachment member having an upper end and a lower end, wherein the lower end is pivotably attached to a first location on the foot unit; and an actuator operatively coupled to the foot unit and to the attachment member, wherein the actuator is configured to actively adjust an angle between the attachment member and the foot unit. For example, the foot unit may be a prosthetic or orthotic device.

Another embodiment of the invention includes a prosthetic system for mimicking the natural movement of an ankle. In one embodiment, the prosthetic system comprises a prosthetic foot; a pivot assembly attached to a first position on the prosthetic foot, wherein the first position is near a natural ankle location of the prosthetic foot; a lower limb member extending in a tibial direction, the lower limb member having an upper end and a lower end, wherein the lower end of the lower limb member is operatively coupled to the pivot assembly; and an actuator operatively coupled to the prosthetic foot and to the lower limb member, wherein the actuator is configured to actively adjust an angle between the lower limb member and the prosthetic foot about the pivot assembly.

One embodiment of the invention includes a method for controlling a device associated with the movement of a limb. In one embodiment, the method comprises monitoring with at least one sensor the movement of an actuatable device associated with a limb; generating data indicative of said movement; processing the data with a processing module to determine a current state of locomotion of the actuatable device; and adjusting the actuatable device based on the determined state of locomotion, wherein said adjusting comprises substantially mimicking the movement of a healthy ankle. For example, the actuatable device may be a prosthesis or an orthosis.

Another embodiment of the invention includes a method for controlling a prosthetic ankle device. In one embodiment, the method comprises monitoring with at least one sensor the movement of an actuatable prosthetic ankle device, wherein the at least one sensor generates data indicative of the movement of the prosthetic ankle device; receiving and processing the data with a control module to determine a current state of locomotion of the actuatable prosthetic ankle device; outputting with the control module at least one control signal based on the determined state of locomotion; and adjusting the actuatable prosthetic ankle device based at least upon the control signal, wherein said adjusting comprises substantially mimicking the movement of a healthy ankle.

In one embodiment, a prosthetic or orthotic system is provided having an ankle-motion-controlled foot. The prosthetic or orthotic system comprises, among other things, a lower limb member, an actuator, and a foot unit. The actuator is configured to mimic the motion of an ankle by adjusting the angle between the lower limb member and the foot unit. The prosthetic or orthotic system also comprises an attachment portion that facilitates coupling of the lower limb member to another prosthetic or orthotic member, to the stump of an amputee, or to another component. The prosthetic or orthotic system may also comprise a rechargeable battery to provide power to the actuator or other components of the system. Embodiments of the invention include systems for both transtibial and transfemoral amputees.

In another embodiment of the invention, the prosthetic or orthotic system comprises a sensor system that is used to capture information regarding the position and movement of the prosthetic or orthotic device. This information may be processed in real-time so as to predict appropriate movements for the prosthetic or orthotic device and to adjust the prosthetic or orthotic device accordingly.

In one embodiment of the invention, a system architecture is provided having a sensor module, a central processing unit, a memory, an external interface, a control drive module, an actuator, and an ankle device. The system architecture may receive instructions and/or data from external sources, such as a user or an electronic device, through the external interface.

In one embodiment, a control system may also be provided that manages the movement of the orthosis or the prosthesis. In one embodiment, the control system manages the movement of an actuator, such as a screw motor. Such motion control provides for movement by the user up inclined surfaces, down declines, or on stairs. In one embodiment, the control system may be configured to monitor through sensors the movements of a healthy limb and use the measurements to control the movement of the prosthesis or orthosis. The control system may also manage the damping of the actuator or other portions of the orthosis or prosthesis.

In one embodiment, a method is provided for controlling actuation of a prosthetic or orthotic device. The method comprises providing one or more sensors on an actuatable prosthetic or orthotic device. Data received from the sensors is processed and is used to determine the current state of locomotion for the prosthetic device. A processing unit, using at least a portion of the data received from the sensors, then predicts movement of the prosthetic or orthotic device. In one embodiment, a prosthetic ankle is provided that mimics the movement of a healthy ankle. The one or more sensors may comprise, for example, gyroscopes and/or accelerometers. In another embodiment of the invention, adjustments are not made to the actuatable prosthetic or orthotic device unless the locomotion type of the user is determined by the processing unit to have a security factor above a predetermined threshold value.

In another embodiment, a method is provided for identifying motion of an orthotic or prosthetic device. The method comprises receiving data from one or more sensors placed on an orthotic or prosthetic device while the device is moving. A waveform is generated from the data received by the sensors. A specific motion for the orthotic or prosthetic device is identified by correlating the waveform with known waveforms for particular types of motion. For example, known waveforms may be inputted by a user or downloaded from an external device or system. The waveforms may also be stored in a memory on the prosthetic or orthotic device.

In another embodiment, a method is provided for actuating an ankle-assisting device. The device is actuated by providing a computer control to provide relative motion between a first and a second portion of the device. In one embodiment, the device is an orthosis. In another embodiment, the device is a prosthesis. In one embodiment, the computer control predicts future motion of the device. In another embodiment, the computer control receives input from at least one sensor module that receives information regarding environmental variables and/or the movement or position of the prosthetic or orthotic device. In another embodiment, the computer control receives input from at least one sensor module that receives information regarding the movement or position of a healthy limb.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 10 is a table illustrating control signals usable to adjust the ankle angle of a prosthetic or orthotic system according to one embodiment of the invention.

DETAILED DESCRIPTION OF THE PREFERRED EMBODIMENTS

Figure 1:
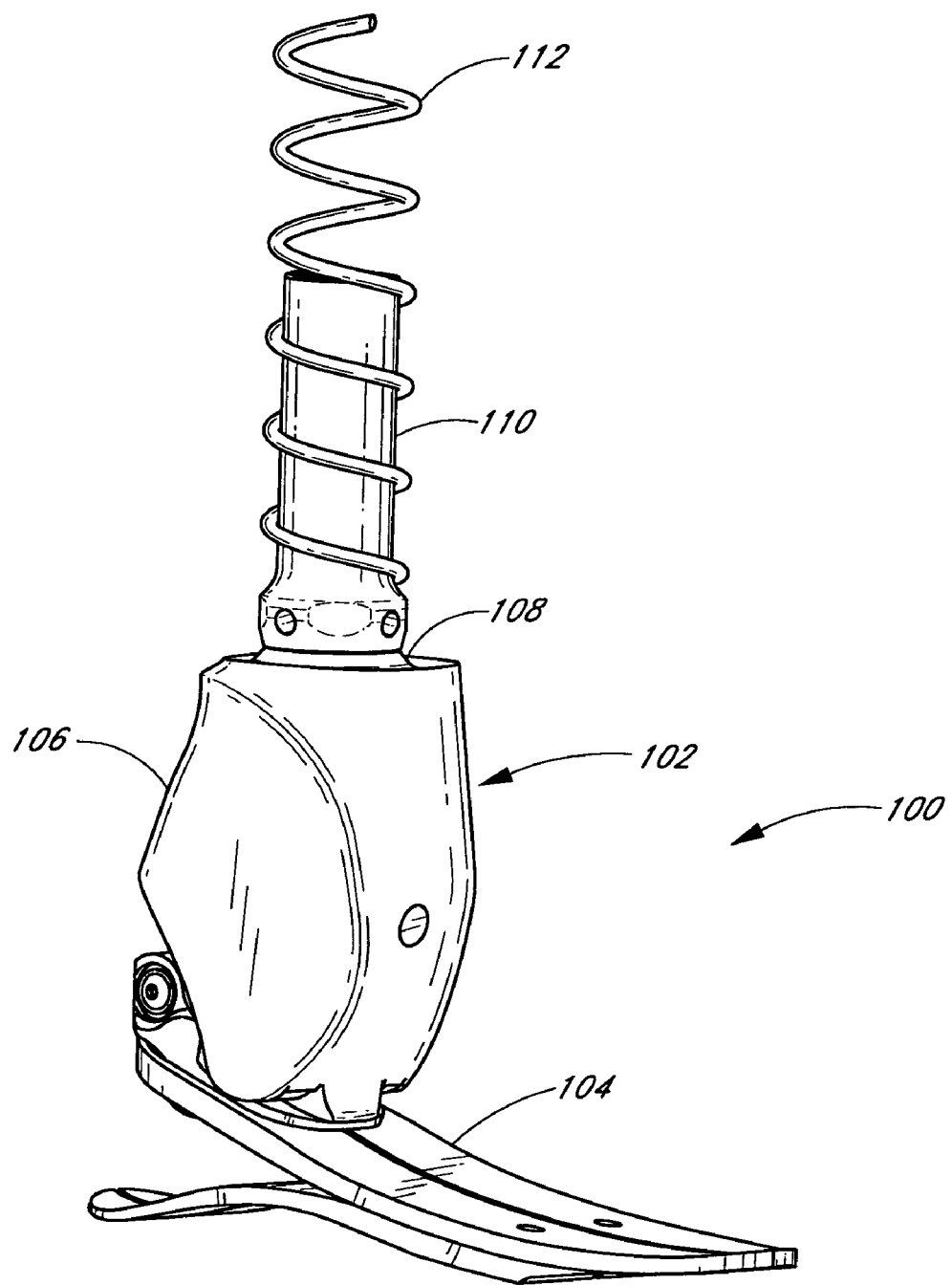
FIG. 1 is a perspective view of a lower limb prosthesis having an ankle-motion-controlled foot unit according to one embodiment of the invention.

Some preferred embodiments of the invention described herein relate generally to prosthetic and orthotic systems and, in particular, to prosthetic and orthotic devices having an ankle-motion-controlled foot. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The features of the system and method will now be described with reference to the drawings summarized above. Throughout the drawings, reference numbers are re-used to indicate correspondence between referenced elements. The drawings, associated descriptions, and specific implementation are provided to illustrate embodiments of the invention and not to limit the scope of the invention.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "ankle device" as used herein is a broad term and is used in its ordinary sense and relates to any prosthetic, orthotic or ankle-assisting device.

The term "transtibial" as used herein is a broad term and is used in its ordinary sense and relates to without limitation any plane, direction, location, or cross-section that is located at or below a knee joint of a body, including artificial knee joints.

The term "transfemoral" as used herein is a broad term and is used in its ordinary sense and relates to without limitation any plane, direction, location, or cross-section that is located at or above a knee joint of a body, including artificial knee joints.

The term "sagittal" as used herein is a broad term and is used in its ordinary sense and relates to any description, location, or direction relating to, situated in, or being in or near the median plane (i.e., the plane divides the body lengthwise into right and left halves) of the body or any plane parallel or approximately parallel thereto. A "sagittal plane" may also refer to any vertical anterior to posterior plane that passes through the body parallel or approximately parallel to the median plane and that divides the body into equal or unequal right and left sections.

The term "coronal" as used herein is a broad term and is used in its ordinary sense and relates to any description, location, or direction relating to, situated in, or being in or near the plane that passes through the long axis of the body. A "coronal plane" may also refer to any plane that passes vertically or approximately vertically through the body and is perpendicular or approximately perpendicular to the median plane and that divides the body into anterior and posterior sections.

FIG. 1 illustrates one embodiment of a lower limb prosthesis 100 having an ankle-motion-controlled foot with an attachment member. The prosthesis 100 comprises an attachment member, in the form of a lower limb member 102, operatively coupled to a foot unit 104. As used herein, the term "attachment member" is a broad term and is used in its ordinary sense and in a prosthetic foot embodiment relates to, without limitation, any member that attaches either directly or indirectly to the foot unit 104 and is moveable in relation thereto, for example by a pivoting motion, and is used to attach the prosthesis 100 to a stump or intermediate prosthesis. As illustrated, the attachment member may take the form of a lower limb member in an ankle-prosthesis embodiment. In other embodiments, for example an orthotic embodiment, the attachment member may be used to attach to and support a body part, such as with a brace, which also is moveably connected to a second member, such as a foot unit, which would also attach to and support a body part, such as the foot. In one embodiment, the lower limb member 102 is a generally elongated member with a main longitudinal axis that extends in approximately a tibial direction, that is, a direction that extends generally along the axis of a natural tibia bone. For example, FIG. 1 depicts the lower limb member 102 as being a generally vertical orientation.

In another embodiment, the lower limb member 102 may comprise multiple sections. For example, the lower limb member 102 may comprise two elongated sections that extend approximately parallel in a tibial direction and that are connected together. In another embodiment, the lower limb member 102 comprises a two-sided chamber having two substantially symmetrical parts to form a partially enclosed housing. In another embodiment, the lower limb member 102 may comprise a hollow member, such as a tube-like structure. In other embodiments, the lower limb member 102 may comprise elongated flat portions or rounded portions. In yet other embodiments, the structure of the lower limb member 102 is not elongated. For example, the lower limb member 102 may comprise a generally circular, cylindrical, half-circular, dome-shaped, oval or rectangular structure. One example of a possible lower limb member is the ankle module and the structures described in U.S. patent application Ser. No. 10/742,455, filed Dec. 18, 2003, and entitled "PROSTHETIC FOOT WITH ROCKER MEMBER," the entirety of which is hereby incorporated herein by reference and is to be considered as part of this specification.

In one embodiment, the lower limb member 102 is generally formed of a machine metal, such as aluminum, or a carbon fiber material. In other embodiments of the invention, the lower limb member 102 may comprise other materials that are suitable for prosthetic devices. In one embodiment, the lower limb member 102 advantageously has a height between approximately 12 and 15 centimeters. In other embodiments of the invention, the lower limb member 102 may have a height less than 12 centimeters or height greater than 15 centimeters depending on the size of the user and/or the intended use of the prosthesis 100. For example, the lower limb member 102 may have a height of approximately 20 centimeters.

In one embodiment, the prosthesis 100 is configured such that the main longitudinal axis of the lower limb member 102 is substantially perpendicular to a lower surface of the foot unit 104 when the prosthesis 100 is in a resting position. In another embodiment, the lower limb member 102 may be substantially perpendicular to a level ground surface when the foot unit 104 rests on the ground. Such a configuration advantageously provides a user with increased support and/or stability.

As depicted in FIG. 1, the lower limb member 102 further comprises a cover 106. The cover 106 houses and/or protects the inner components of the lower limb member 102. In another embodiment, the cover 106 may be rounded or may be shaped in the form of a natural human leg.

The lower limb member 102 further comprises an attachment portion 108 to facilitate coupling of the lower limb member 102. For example, as depicted in FIG. 1, the attachment portion 108 of the lower limb member 102 couples the prosthesis 100 to a pylon 110. In other embodiments of the invention, the attachment portion 108 may be configured to couple the prosthesis 100 to a stump of an amputee or to another prosthetic device. FIG. 1 also depicts a control wire 112 usable to provide power to and/or communicate control signals to the prosthesis 100.

The foot unit 104 may comprise various types of prosthetic or orthotic feet. As illustrated in FIG. 1, the foot unit 104 incorporates a design described in Applicant's co-pending U.S. patent application Ser. No. 10/642,125, entitled "LOW PROFILE PROSTHETIC FOOT," and filed Aug. 15, 2003 the entirety of which is hereby incorporated by reference and is to be considered as part of this specification. For example, the foot unit 104 may comprise a standard LP VARI-FLEX® unit available from Össur.

In one embodiment, the foot unit 104 is configured to exert a proportional response to weight or impact levels on the foot unit 104. In addition, the foot unit 104 may comprise shock absorption for comfortable loading of the heel and/or for returning expended energy. The foot unit 104 may comprise a full-length toe lever with enhanced flexibility so as to provide a stride length for the prosthetic limb that mimics the stride length of the healthy limb. In addition, as depicted in FIG. 1, the foot unit 104 may comprise a split-toe configuration, which facilitates movement on uneven terrain. The foot unit 104 may also include a cosmesis or a foot cover such as, for example, a standard Flex-Foot cover available from Össur.

Figure 2:
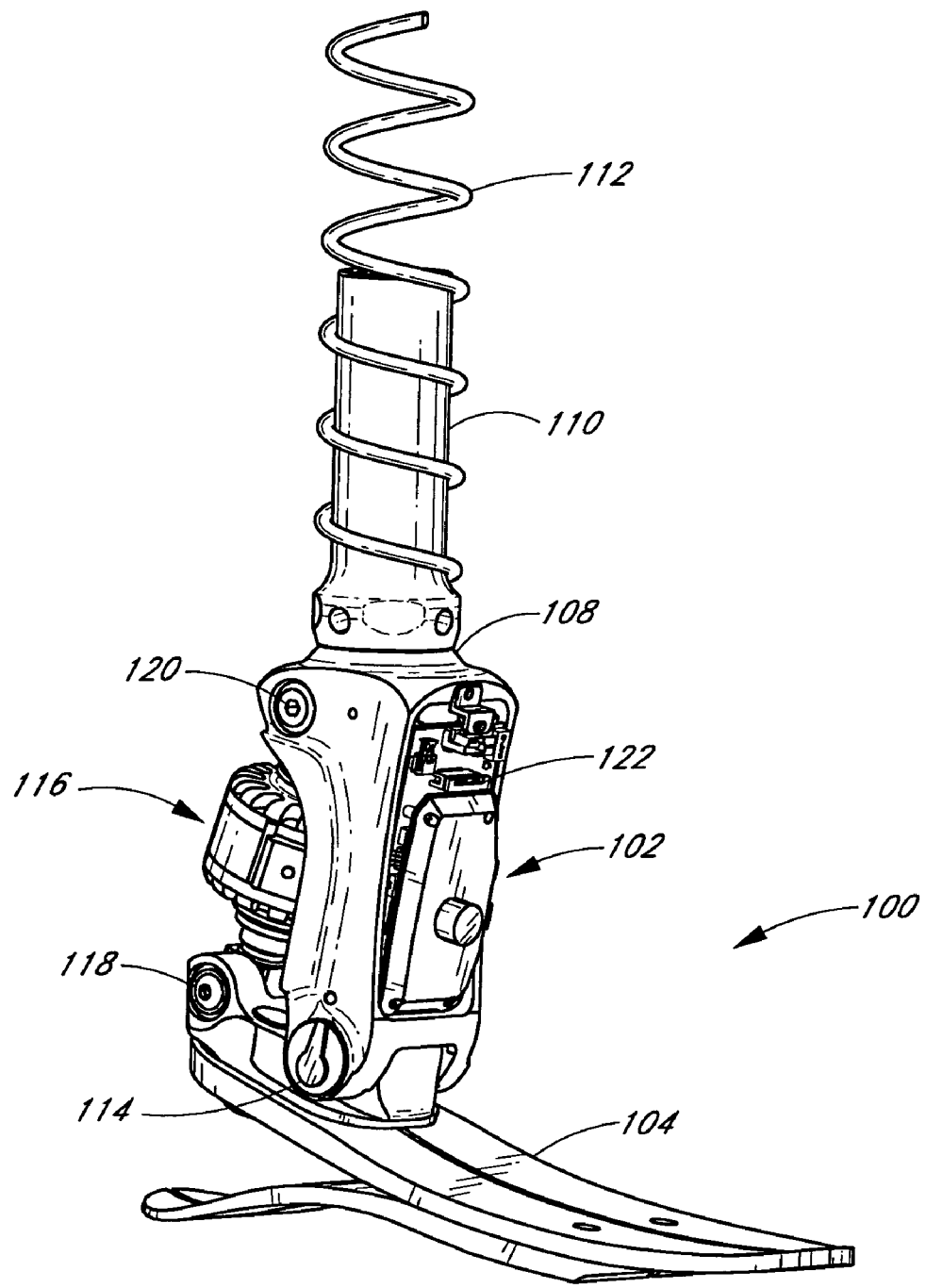
FIG. 2 is a perspective view of the lower limb prosthesis of FIG. 1, wherein a cover is removed to show inner components of the prosthesis.

FIG. 2 depicts the prosthesis 100 with the cover 106 removed. As shown, a lower end of the lower limb member 102 is coupled to the foot unit 104 at a pivot assembly 114. As illustrated, the lower limb member 102 is coupled to an ankle plate of the foot unit 104, which extends generally rearward and upward from a toe portion of the foot unit 104. The pivot assembly 114 allows for angular movement of the foot unit 104 with respect to the lower limb member 102. For example, in one embodiment, the pivot assembly 114 advantageously comprises at least one pivot pin. In other embodiments, the pivot assembly 114 comprises a hinge, a multi-axial configuration, a polycentric configuration, combinations of the same or the like. Preferably, the pivot assembly 114 is located on a portion of the foot unit 104 that is near a natural ankle location of the foot unit 104. In other embodiments of the invention, the pivot assembly 114 may be bolted or otherwise releasably connected to the foot unit 104.

FIG. 2 further depicts the prosthesis 100 having an actuator 116. In one embodiment, the actuator 116 advantageously provides the prosthesis 100 with the necessary energy to execute angular displacements synchronized with the amputee's locomotion. For example, the actuator 116 may cause the foot unit 104 to move similar to a natural human foot. In one embodiment, the lower end of the actuator 116 is coupled to the foot unit 104 at a first attachment point 118. As illustrated, the foot attachment point 118 is advantageously located on the upper surface of the foot unit 104 on a posterior portion thereof. The upper end of the actuator 116 is coupled to the lower limb member 102 at a second attachment point 120.

In one embodiment, the linear motion (or extension and contraction) of the actuator 116 controls, or actively adjusts, the angle between the foot unit 104 and the lower limb member 102. FIG. 2 depicts the actuator 116 comprising a double-screw motor, wherein the motor pushes or pulls a posterior portion of the foot unit 104 with respect to the lower limb member 102. In other embodiments, the actuator 116 comprises other mechanisms capable of actively adjusting an angle, or providing for motion between, multiple members. For example, the actuator 116 may comprise a single-screw motor, a piston cylinder-type structure, a servomotor, a stepper motor, a rotary motor, a spring, a fluid actuator, or the like. In yet other embodiments, the actuator 116 may actively adjust in only one direction, the angle between the lower limb member 102 and the foot unit 104. In such an embodiment, the weight of the user may also be used in controlling the angle caused by and/or the movement of the actuator 116.

FIG. 2 illustrates the actuator 116 in a posterior configuration, wherein the actuator 116 is located behind the lower limb member 102. In other embodiments, the actuator 116 may be used in an anterior configuration, wherein the actuator 116 is located in front of the lower limb member 102. In another embodiment of the invention, the actuator 116 comprises an auto adjusting ankle structure and incorporates a design, such as described in U.S. Pat. No. 5,957,981, the entirety of which is hereby incorporated by reference and is to be considered as a part of this specification. The particular configuration or structure may be selected to most closely imitate the movement and location of a natural human ankle joint and to facilitate insertion of the prosthesis 100 into an outer cosmesis.

Furthermore, the actuator 116 is advantageously configured to operate so as to not to emit loud noises, such as intermittent noises, perceptible by the user and/or others. The actuator 116 may also be configured to not operate or adjust if the prosthesis 100 experiences torque, such as in the sagittal plane, that exceeds a certain level. For example, if the torque level exceeds four Newton meters (Nm), the actuator 116 may cease to operate or may issue an alarm.

The actuator 116 may also be substantially enclosed within the cover 106 as shown in FIG. 1 such that the portions of the actuator 116 are not visible and/or exposed to the environment. In another embodiment, the actuator may be at least partially enclosed by the lower limb member 102.

FIG. 2 further depicts control circuitry 122 usable to control the operation of the actuator 116 and/or the foot unit 104. In one embodiment, the control circuitry 122 comprises at least one printed circuit board (PCB). The PCB may further comprise a microprocessor. Software may also reside on the PCB so as to perform signal processing and/or control the movement of the prosthesis 100.

In one embodiment, the prosthesis 100 includes a battery (not shown) that powers the control circuitry 122 and/or the actuator 116. In one embodiment, the battery comprises a rechargeable lithium ion battery that preferably has a power cycle of at least 12 to 16 hours. In yet other embodiments, the power cycle of the battery may be less than 12 hours or may be more than 16 hours. In other embodiments of the invention, the battery comprises a lithium polymer battery, fuel cell technology, or other types of batteries or technology usable to provide power to the prosthesis 100. In yet other embodiments, the battery is removably attached to a rear surface of the lower limb member 102, to other portions of the prosthesis 100, or is located remote the prosthesis 100. In further embodiments, the prosthesis 100 may be connected to an external power source, such as through a wall adapter or car adapter, to recharge the battery.

In one embodiment, the prosthesis 100 is configured to lock in a neutral position, such as the lower limb member 102 being aligned generally vertical relative to a level ground surface when the foot unit 104 is resting on the level ground surface, when the battery is out of power or enters a low power stage. Such locking provides for operational safety, reliability, and/or stability for a user. The prosthesis 100 may also provide a battery status display that alerts the user as to the status (i.e., charge) of the battery. In another embodiment, the prosthesis 100 locks into a substantially neutral position when the motion control functions of the prosthesis 100 are turned off or disabled by a user.

As discussed above, a cosmesis material or other dressings may be used with the prosthesis 100 so as to give the prosthesis 100 a more natural look or shape. In addition, the cosmesis, dressings, or other filler material may be used to prevent contaminants, such as dirt or water, from contacting the components of the prosthesis 100.

Figure 3:
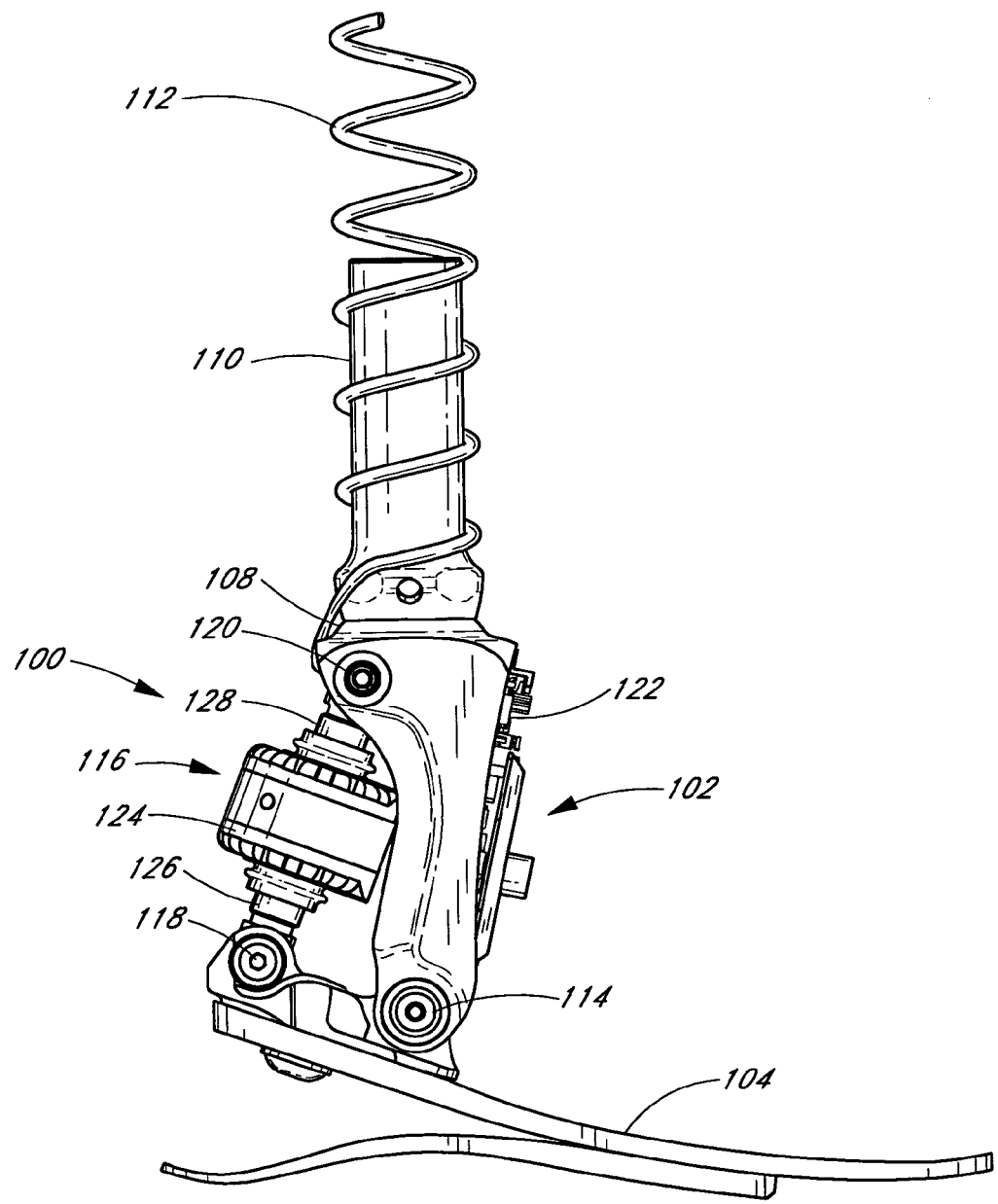
FIG. 3 is a side view of the lower limb prosthesis of FIG. 2.

FIG. 3 depicts a side view of the prosthesis 100 according to one embodiment of the invention. As depicted in FIG. 3, the actuator 116 further comprises a main housing 124, a lower extendable portion 126, and an upper extendable portion 128. The lower extendable portion 126 couples the main housing 124 of the actuator 116 to the foot unit 104 at the first attachment point 118. The upper extendable portion 128 couples the main housing 124 of the actuator 116 to the lower limb member 102 at the second attachment point 120. During operation and active adjustment of the prosthesis 100, the lower extendable portion 126 and/or the upper extendable portion 128 move into and/or out of the main housing 124 of the actuator 116 to adjust an angle between the foot unit 104 and the lower limb member 102.

For example, to increase an angle between the foot unit 104 and the lower limb member 102, the actuator 116 causes the lower extendable portion 126 and/or the upper extendable portion 128 to contract or withdraw into the main housing 124. For example, at least one of the extendable portions 126, 128 may have a threaded surface such that rotation in one direction (e.g., clockwise) causes the extendable portion to withdraw into the main housing 124 of the actuator. In other embodiments, at least one of the extendable portions 126, 128 comprises multiple telescoping pieces such that, upon contraction, one of the multiple pieces of extendable portion contracts into another of the multiple pieces without withdrawing into the main housing 124. Likewise, to decrease an angle between the foot unit 104 and the lower limb member 102, the lower extendable portion 126 and/or the upper extendable portion 128 may extend from the main housing 124.

In embodiments of the invention having an anterior configuration for the actuator 116, extension of the lower extendable portion 126 and/or the upper extendable portion 128 causes an increase in the angle between the lower limb member 102 and the foot unit 104. Likewise, a contraction of the lower extendable portion 126 and/or the upper extendable portion 128 causes a decrease in the angle between the foot unit 104 and the lower limb member 102.

Figure 4:
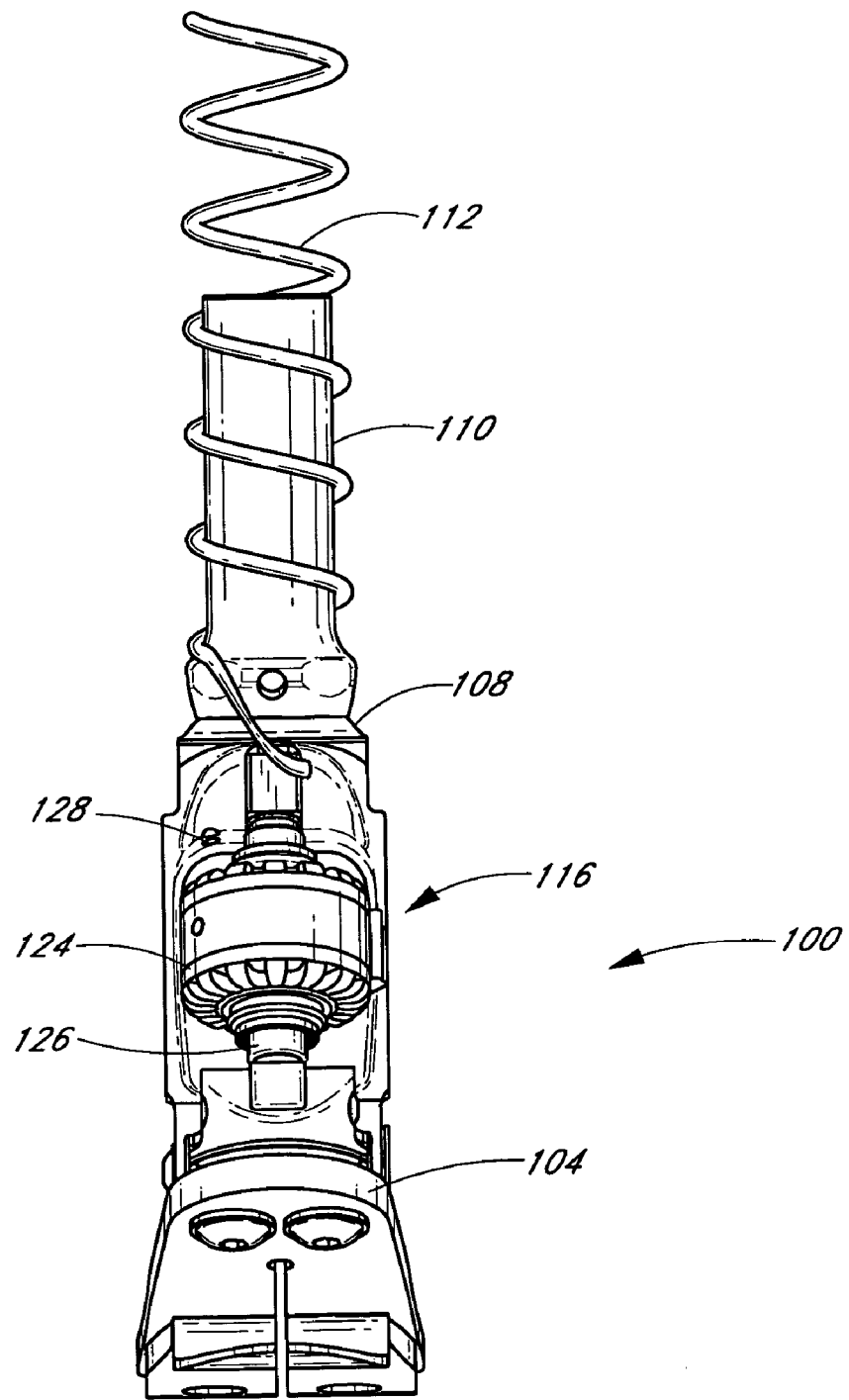
FIG. 4 is a rear view of the lower limb prosthesis of FIG. 2.

FIG. 4 illustrates a rear view of the prosthesis 100 depicted in FIGS. 1-3. In other embodiments of the invention, the cover 106 extends around the posterior portion of the prosthesis 100 to house at least a portion of the actuator 116 such that portions of the actuator 116 are not visible and/or not exposed to the environment.

Figure 5:
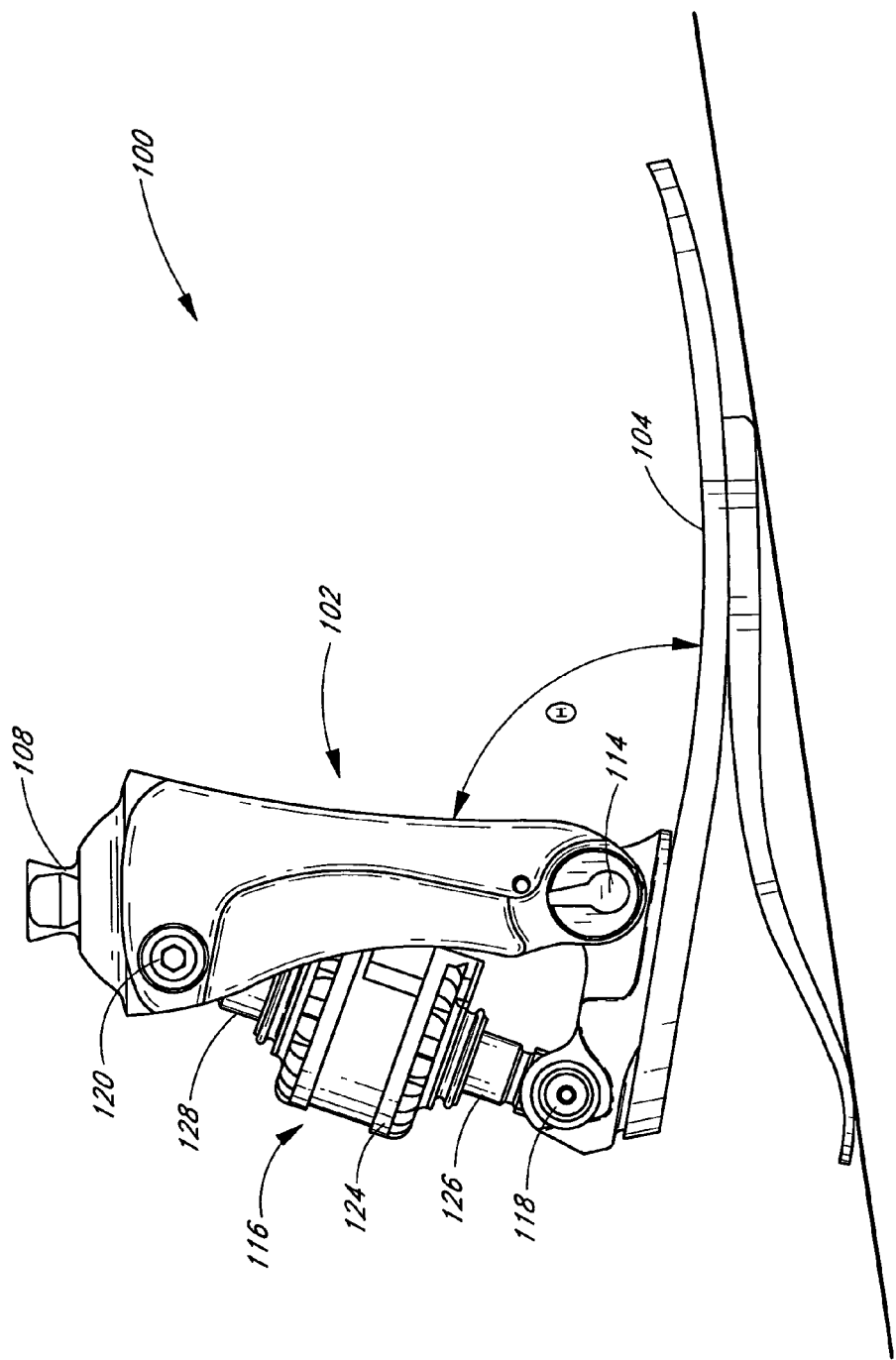
FIG. 5 is a side view of the lower limb prosthesis of FIG. 1 with the cover shown partially removed, wherein the ankle-motion-controlled foot is adjusted to accommodate an incline.
Figure 6:
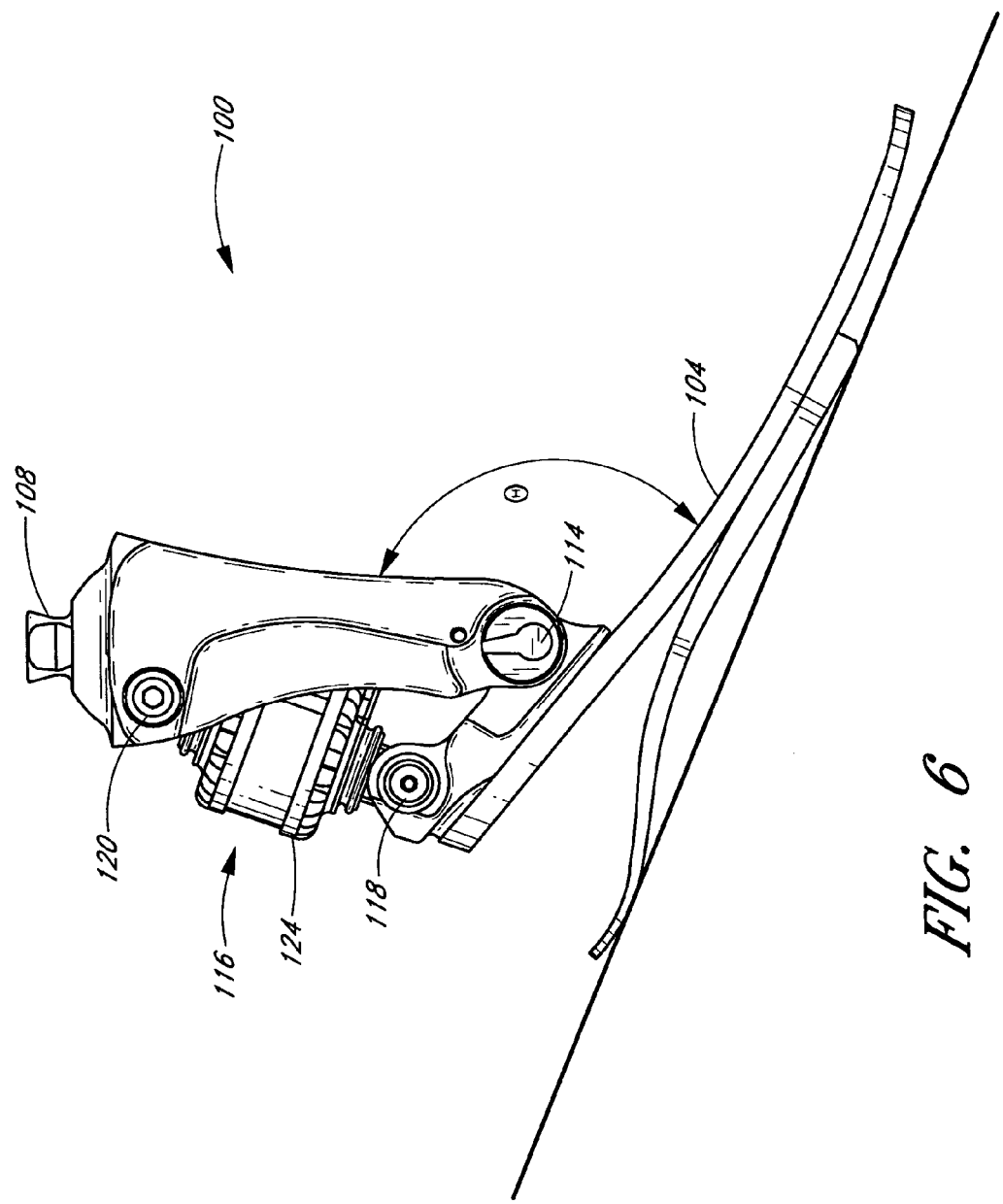
FIG. 6 is a side view of a lower limb prosthesis of FIG. 5, wherein the ankle-motion-controlled foot is adjusted to accommodate a decline.

FIGS. 5 and 6 illustrate one embodiment of the prosthesis 100 as it adjusts to inclines and declines. With reference to FIG. 5, the prosthesis 100 is depicted as adjusting to an incline. In this embodiment, the actuator 116 extends so as to decrease an angle θ between the lower limb member 102 and the foot unit 104 (or "dorsiflexion"). With respect to dorsiflexion, in one embodiment, the angular range of motion of the prosthesis 100 is from about 0 to 10 degrees from the neutral position. Other embodiments may also facilitate exaggerated dorsiflexion during swing phase.

FIG. 6 illustrates the prosthesis 100 as it adjusts to a decline. The actuator 116 extends so as to increase the angle θ between the lower limb member 102 and the foot unit 104 (or "plantarflexion"). With respect to plantarflexion, in one embodiment, the angular range of motion of the prosthesis 100 is from about 0 to 20 degrees from the neutral position. Such plantarflexion mimics natural ankle movement and provides for greater stability to an amputee or a user. In one embodiment, the total range of motion about the ankle pivot axis of the prosthesis 100, including both plantarflexion and dorsiflexion, is approximately 30 degrees or more.

In addition to operating on inclines and declines, the motion-controlled foot of the prosthesis 100 advantageously accommodates different terrain, operates while traveling up and down stairs, and facilitates level ground walking. In addition, the prosthesis 100 may provide for automatic heel height adjustability. Heel height may be measured, in one embodiment, from an ankle portion of the lower limb member 102 to a ground surface when the foot unit 104 is generally flat to the ground. For example, a user may adjust to various heel heights, such as through pressing one or more buttons, such that the prosthesis 100 automatically aligns itself to the appropriate heel height. In one embodiment, the prosthesis 100 includes a plurality of predetermined heel heights. In yet other embodiments, the prosthesis 100 may automatically adjust the heel height without the need for user input.

FIGS. 5 and 6 further illustrate one embodiment of the attachment portion 108. The attachment portion 108 provides alignment between the natural limb of the amputee and the prosthesis 100 and may be configured so as to decrease pressure peaks and shear forces. For example, the attachment portion 108 may be configured to attach to another prosthesis, to the stump of the amputee, or to another component. In one embodiment, the attachment portion 108 comprises a socket connector. The socket connector may be configured to receive a 32 mm-thread component, a male pyramid type coupler, or other components. In other embodiments, the attachment portion 108 may also comprise, or be configured to receive, a female pyramid adapter.

Figure 7:
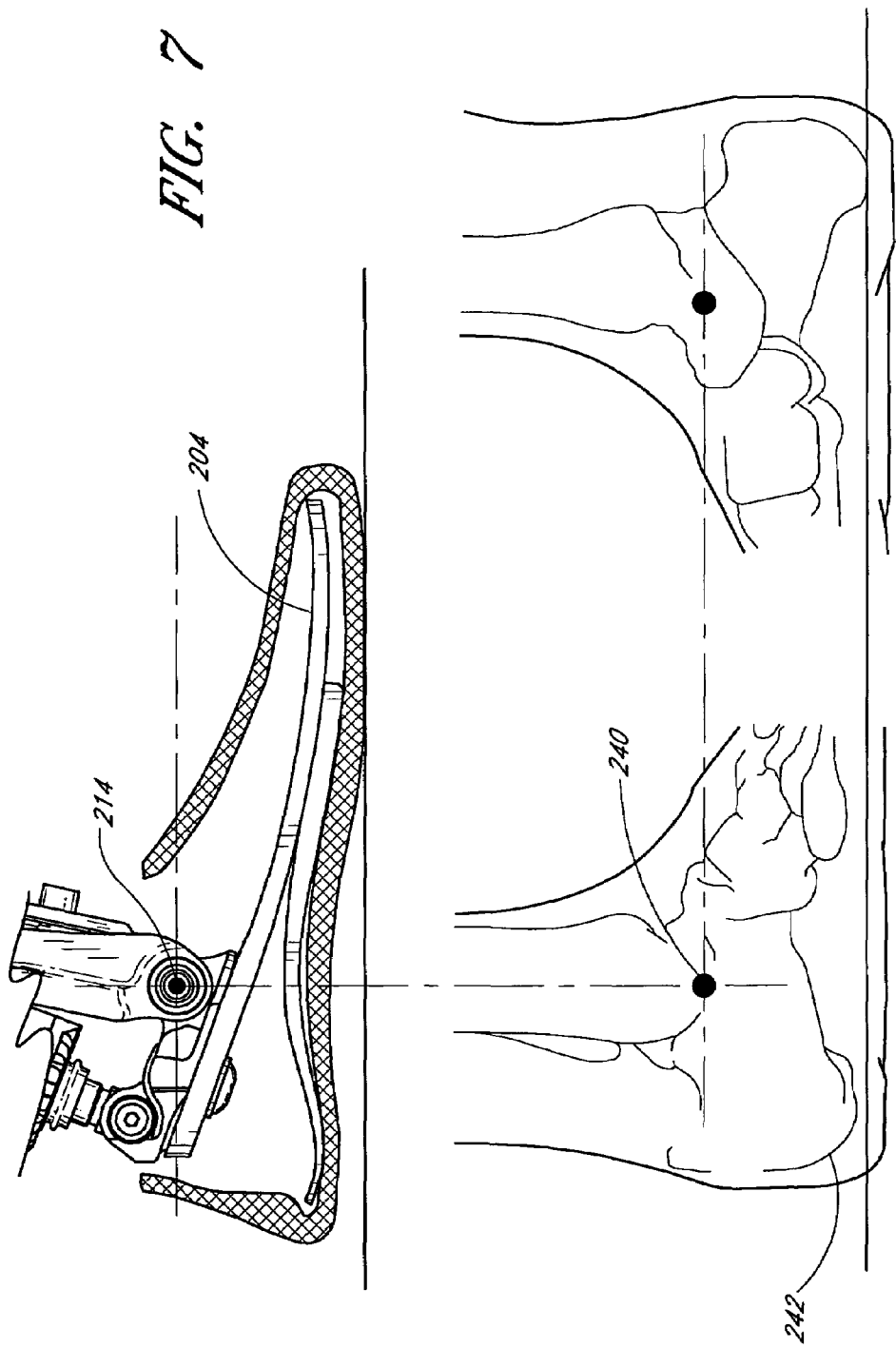
FIG. 7 is a schematic drawing indicating the correlation between an ankle pivot point on an exemplifying embodiment of a prosthetic foot unit with the natural ankle joint of a human foot.

As depicted in FIGS. 5 and 6, the pivot assembly 114 is positioned to mimic a normal human ankle axis. FIG. 7 further illustrates a schematic drawing indicating the correlation between an ankle pivot point on a prosthetic foot unit 204 with the natural human ankle joint of a foot. In particular, the prosthetic foot unit 204 comprises a pivot assembly 214 that corresponds to an ankle joint 240 of a human foot 242. For example, in one embodiment of the invention, the pivot assembly 114 is located near the mechanical ankle center of rotation of the prosthesis 100.

Figure 8:
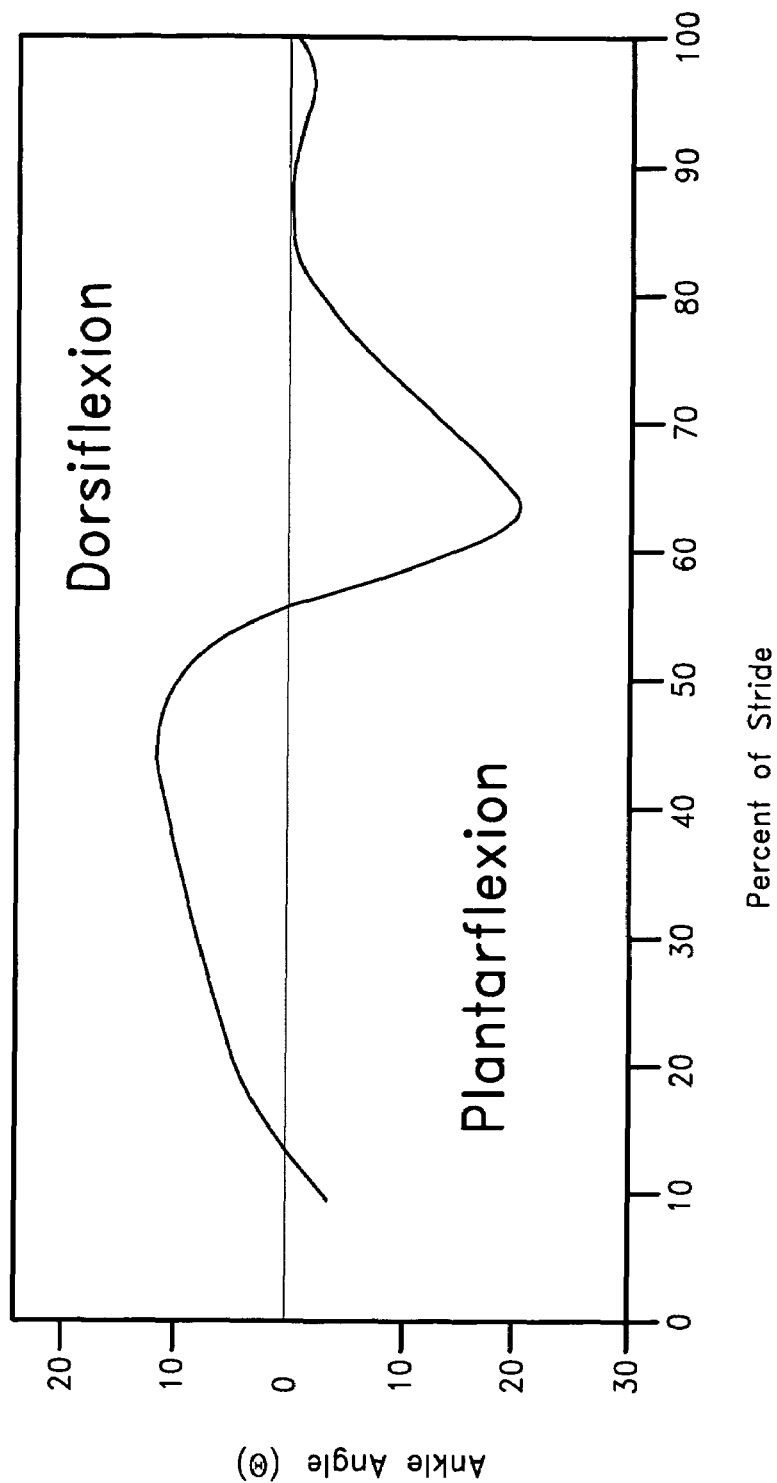
FIG. 8 is a graph depicting the range of ankle motion of an exemplifying embodiment of a prosthetic or orthotic system during one full stride on a level surface.

FIG. 8 illustrates a graph depicting the possible range of ankle motion of an embodiment of the prosthesis 100 during one full stride on a level surface. As shown, the x-axis of the graph represents various points during one full stride of a user (i.e., 0 to 100 percent). The y-axis represents the ankle angle (Δ) of the prosthesis 100 relative to the ankle angle when the prosthesis is in a neutral position. During one full stride, the ankle angle (Δ) varies from approximately 20 degrees plantarflexion (i.e., neutral position angle +20 degrees) to approximately 10 degrees dorsiflexion (i.e., neutral position angle −10 degrees).

In embodiments as described above, no dampening is provided when adjusting the angular range of motion. In another embodiment of the invention, the prosthesis 100 is configured to provide dampening or passive, soft resistance to changes in the angle between the lower limb member 102 and the foot unit 104. An example of a system for controlling such dampening is disclosed in U.S. Pat. No. 6,443,993, which is hereby incorporated herein by reference and is to be considered as a part of this specification.

For example, when the user is in a standing position, the actuator 116 may provide for increased resistance, or dampening, so as to provide stability to the user. In one embodiment of the invention, dampening of the prosthesis 100 may be provided by hydraulic dampers. In other embodiments of the invention, other components or devices that are known in the art may be used to provide dampening for the prosthesis 100. In addition, in one embodiment of the invention, the dampers may be dynamically controlled, such as through an electronic control system, which is discussed in more detail below. In yet other embodiments, the dampers may be controlled through mechanical and/or fluid-type structures.

It is also recognized that, although the above description has been directed generally to prosthetic systems and devices, the description may also apply to an embodiment of the invention having an orthotic system or device. For example, in one embodiment of the invention, an orthotic system may comprise at least one actuator that actively controls the angle of an orthosis that is used with an injured or debilitated ankle. In addition, the orthotic system may, in addition to the electronic control of the orthotic system, provide for the user's control or natural movement of the injured ankle or leg.

In addition, the above-described systems may be implemented in prosthetic or orthotic systems other than transtibial, or below-the-knee, systems. For example, in one embodiment of the invention, the prosthetic or orthotic system may be used in a transfemoral, or above-the-knee, system, such as is disclosed in U.S. Provisional Application No. 60/569,512, filed May 7, 2004, and entitled "MAGNETORHEOLOGICALLY ACTUATED PROSTHETIC KNEE" and U.S. Provisional Application No. 60/624,986, filed Nov. 3, 2004, and entitled "MAGNETORHEOLOGICALLY ACTUATED PROSTHETIC KNEE", each of which is hereby incorporated herein by reference in its entirety and is to be considered as part of this specification. For example, the prosthetic or orthotic system may include both a prosthetic or orthotic ankle and/or a prosthetic or orthotic knee.

Figure 9:
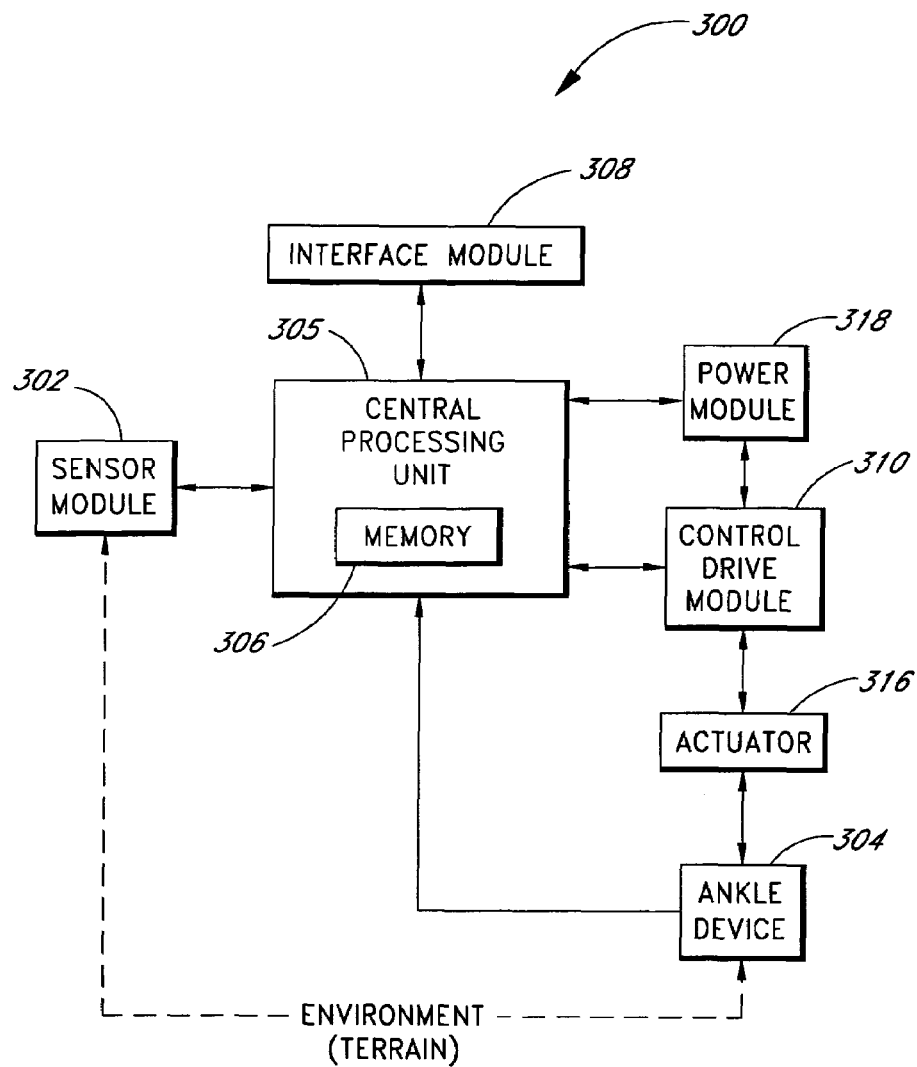
FIG. 9 is a block diagram of an exemplifying embodiment of a control system architecture of a prosthetic or orthotic system having an ankle-motion-controlled foot.

FIG. 9 illustrates a block diagram of one embodiment of a system architecture of a control system 300 for an ankle-motion-controlled foot. In one embodiment of the invention, the control system 300 is usable by the lower limb prosthesis 100 depicted in FIGS. 1-6. In other embodiments of the invention the control system 300 is usable by an orthotic system or a rehabilitation system having an ankle-motion-controlled foot, or other motion-controlled limb. In one embodiment, the control system 300 is based on a distributed processing system wherein the different functions performed by the prosthetic or orthotic system, such as sensing, data processing, and actuation, are performed or controlled by multiple processors that communicate with each other. With reference to FIG. 9, the control system 300 includes a sensor module 302, an ankle device 304 (such as, for example, the prosthesis 100 depicted in FIG. 1), a central processing unit ("CPU") 305, a memory 306, an interface module 308, a control drive module 310, an actuator 316 and a power module 318.

In one embodiment, the control system 300 depicted in FIG. 9 processes data received from the sensing module 302 with the CPU 305. The CPU 305 communicates with the control drive module 310 to control the operation of the actuator 316 so as to mimic natural ankle movement by the ankle device 304. Furthermore, the control system 300 may predict how the ankle device 304 may need to be adjusted in order to accommodate movement by the user. The CPU 305 may also receive commands from a user and/or other device through the interface module 308. The power module 318 provides power to the other components of the control system 300. Each of these components is described in more detail below.

In one embodiment, the sensor module 302 is used to measure variables relating to the ankle device 304, such as the position and/or the movement of the ankle device 304 throughout a gait cycle. In such an embodiment the sensor module 320 is advantageously located on the ankle device 304. For example, the sensor module 302 may be located near a mechanical ankle center of rotation of the ankle device 304, such as the pivot assembly 114 of the prosthesis 100 depicted in FIG. 2. In another embodiment, the sensor module 302 may be located on the user's natural limb that is attached to, or associated with, the ankle device 304. In such an embodiment, the sensors are used to capture information relating to the movement of the natural limb on the user's ankle-device side to adjust the ankle device 304.

In one embodiment, the sensor module 302 advantageously includes a printed circuit board housing, multiple sensors, such as accelerometers, which each measures an acceleration of the ankle device 304 in a different axis. For example, the sensor module 302 may comprise three accelerometers that measure acceleration of the ankle device 304 in three substantially, mutually perpendicular axes. Sensors of the type suitable for the sensor module 302 are available from, for example, Dynastream Innovations, Inc. (Alberta, Canada).

In other embodiments, the sensor module 302 may include one or more other types of sensors in combination with, or in place of, accelerometers. For example, the sensor module 302 may include a gyroscope configured to measure the angular speed of body segments and/or the ankle device 304. In other embodiments, the sensor module 302 includes a plantar pressure sensor configured to measure, for example, the vertical plantar pressure of a specific underfoot area. In yet other embodiments, the sensor module 302 may include one or more of the following: kinematic sensors, single-axis gyroscopes, single- or multi-axis accelerometers, load sensors, flex sensors or myoelectric sensors that may be configured to capture data from the user's natural limb. U.S. Pat. No. 5,955,667, U.S. Pat. No. 6,301,964, and U.S. Pat. No. 6,513,381, also illustrate examples of sensors that may be used with embodiments of the invention, which patents are herein incorporated by reference in their entireties and are to be considered as part of this specification.

Furthermore, the sensor module 302 may be used to capture information relating to, for example, one or more of the following: the position of the ankle device 304 with respect to the ground; the inclination angle of the ankle device 304; the direction of gravity with respect to the position of the ankle device 304; information that relates to a stride of the user, such as when the ankle device 304 contacts the ground (e.g., "heel strike"), is in mid-stride, or leaves the ground (e.g., "toe-off"), the distance from the ground of the prosthesis 100 at the peak of the swing phase (i.e., the maximum height during the swing phase); the timing of the peak of the swing phase; and the like.

In yet other embodiments, the sensor module 302 is configured to detect gait patterns and/or events. For example, the sensor module 302 may determine whether the user is in a standing/stopped position, is walking on level ground, is ascending and/or descending stairs or sloped surfaces, or the like. In other embodiments, the sensor module 302 is configured to detect or measure the heel height of the ankle device 304 and/or determine a static shank angle in order to detect when the user is in a sitting position.

As depicted in FIG. 9, in one embodiment of the invention, the sensor module 302 is further configured to measure environmental or terrain variables including one or more of the following: the characteristics of the ground surface, the angle of the ground surface, the air temperature and wind resistance. In one embodiment, the measured temperature may be used to calibrate the gain and/or bias of other sensors.

In other embodiments, the sensor module 302 captures information about the movement and/or position of a user's natural limb, such as a healthy leg. In such an embodiment, it may be preferable that when operating on an incline or a decline, the first step of the user be taken with the healthy leg. Such would allow measurements taken from the natural movement of the healthy leg prior to adjusting the ankle device 304. In one embodiment of the invention, the control system 300 detects the gait of the user and adjusts the ankle device 304 accordingly while the ankle device 304 is in a swing phase of the first step. In other embodiments of the invention, there may be a latency period in which the control system 300 requires one or two strides before being able to accurately determine the gait of the user and to adjust the ankle device 304 appropriately.

In one embodiment of the invention, the sensor module 302 has a default sampling rate of 100 hertz (Hz). In other embodiments, the sampling rate may be higher or lower than 100 Hz or may be adjustable by a user, or may be adjusted automatically by software or parameter settings. In addition, the sensor module 302 may provide for synchronization between types of data being sensed or include time stamping. The sensors may also be configured so as to have an angular resolution of approximately 0.5 degrees, allowing for fine adjustments of the ankle device 304.

In one embodiment, the sensor module 302 is configured to power down into a "sleep" mode when sensing is not needed, such as for example, when the user is relaxing while in a sitting or reclining position. In such an embodiment, the sensor module 302 may awake from the sleep state upon movement of the sensor module 302 or upon input from the user. In one embodiment, the sensor module 302 consumes approximately 30 milliamps (mA) when in an "active" mode and approximately 0.1 mA when in a "sleep" mode.

FIG. 9 illustrates the sensor module 302 communicating with the CPU 305. In one embodiment, the sensor module 302 advantageously provides measurement data to the CPU 305 and/or to other components of the control system 300. In one embodiment, the sensor module 302 is coupled to a transmitter, such as, for example, a Bluetooth® transmitter, that transmits the measurements to the CPU 305. In other embodiments, other types of transmitters or wireless technology may be used, such as infrared, WiFi®, or radio frequency (RF) technology. In other embodiments, wired technologies may be used to communicate with the CPU 305.

In one embodiment, the sensor module 302 sends a data string to the CPU 305 that comprises various types of information. For example, the data string may comprise 160 bits and include the following information:
[TS; AccX; AccY; AccZ; GyroX, GyroY, GyroZ, DegX, DegY, FS, M];
wherein TS=Timestamp; AccX=linear acceleration of foot along X axis; AccY=linear acceleration of foot along Y axis; AccZ=linear acceleration of foot along Z axis; GyroX=angular acceleration of foot along X axis; GyroY=angular acceleration of foot along Y axis; GyroZ=angular acceleration of foot along Z axis; DegX=foot inclination angle in coronal plane; DegY=foot inclination angle in sagittal plane; FS=logic state of switches in the ankle device 304; and M=orientation of the sensors. In other embodiments of the invention, other lengths of data strings comprising more or less information may be used.

The CPU 305 advantageously processes data received from other components of the control system 300. In one embodiment of the invention, the CPU 305 processes information relating to the gait of the user, such as information received from the sensor module 302, determines locomotion type (i.e., gait pattern), and/or sends commands to the control drive module 310. For example, the data captured by the sensor module 302 may be used to generate a waveform that portrays information relating to the gait or movement of the user. Subsequent changes to the waveform may be identified by the CPU 305 to predict future movement of the user and to adjust the ankle device 304 accordingly. In one embodiment of the invention, the CPU 305 may detect gait patterns from as slow as 20 steps per minute to as high as 125 steps per minute. In other embodiments of the invention, the CPU 305 may detect gait patterns that are slower than 20 steps per minute or higher than 125 steps per minute.

In one embodiment of the invention, the CPU 305 processes data relating to state transitions according to the following table (TABLE 1). In particular, TABLE 1 shows possible state transitions usable with the control system 300. The first column of TABLE 1 lists possible initial states of the ankle device 304, and the first row lists possible second states of the ankle device 304. The body of TABLE 1 identifies the source of data used by the CPU 305 in controlling, or actively adjusting, the actuator 316 and the ankle device 304 during the transition from a first state to a second state; wherein "N" indicates that no additional data is needed for the state transition; "L" indicates that the CPU 305 uses transition logic to determine the adjustments to the ankle device 304 during the state transition; and "I" indicates the CPU receives data from an interface (e.g., interface module 308, external user interface, electronic interface or the like). Transition logic usable with embodiments of the invention may be developed by one with ordinary skill in the relevant art. Examples of transition logic used in similar systems and methods to embodiments of the present invention are disclosed in U.S. Provisional Application No. 60/572,996, entitled "CONTROL SYSTEM AND METHOD FOR A PROSTHETIC KNEE," filed May 19, 2004, which is hereby incorporated herein by reference and is to be considered as a part of this specification.

TABLE 1

| TRANSITIONS FROM STATE TO STATE | OFF | HEEL_ HEIGHT _CAL | SENSOR_CAL | NEUTRAL | WALK | STAIRS_UP | STAIRS_DOWN | RELAX | PANTS |
| --- | --- | --- | --- | --- | --- | --- | --- | --- | --- |
| OFF | | N | I | I | I | N | N | N | I | I |
| HEEL_HEIGHT_CAL | L | N | N | L | N | N | N | N | N |
| SENSOR_CAL | L | N | N | L | N | N | N | N | N |
| NEUTRAL | I | I | I | N | L | L | L | L | I |
| WALK | I | N | N | L | N | L | L | N | N |
| STAIRS_UP | I | N | N | L | L | N | L | N | N |
| STAIRS_DOWN | I | N | N | L | L | L | N | N | N |
| RELAX | I | N | N | L | N | N | N | N | I |
| PANTS | I | N | N | I | N | N | N | N | N |

In one embodiment, the above described states in TABLE 1 are predefined states of the ankle device 304. For example, the "OFF" state may indicate that the functions of the ankle device 304 and the actuator 316 are in an off or suspend mode. The "HEEL_HEIGHT_CAL" state relates to the measuring of a heel height from a static sensor angle such as, for example, when the ankle device 304 is not in motion. The "SENSOR_CAL" state relates to surface angle calibration when the user is walking on a level surface. The "NEUTRAL" state relates to when the ankle device 304 is locked in a substantially fixed position. The "WALK" state relates to when the user is walking, such as on a level or sloped surface. "The "STAIRS_UP" and "STAIRS_DOWN" states relate to when the user is walking, respectively, up and down stairs. The "RELAX" state relates to when the user is in a relaxed position. For example, in one embodiment, the "RELAX" state relates to when a user is in a sitting position with the limb having the ankle device 304 crossed over the other limb. In such an embodiment, the control system 300 may cause the ankle device 304 to move into a maximum plantarflexion position to mimic, for example, the natural position and/or look of a healthy foot. The "PANTS" state relates to when a user is putting on pants, trousers, shorts or the like. In such a state, the control system 300 may, in one embodiment, cause the ankle device 304 to move into a maximum plantarflexion position to facilitate putting the clothing on over the ankle device 304.

In other embodiments of the invention, other states are usable with the ankle device 304 in place of, or in combination with, the states identified in TABLE 1. For example, states may be defined that correspond to lying down, cycling, climbing a ladder or the like. Furthermore, in controlling the state transitions, the CPU 305 and/or control system 300 may process or derive data from sources other than those listed in TABLE 1.

In other embodiments, the CPU 305 may perform a variety of other functions. For example, the CPU 305 may use information received from the sensor module 302 to detect stumbling by the user. The CPU 305 may function as a manager of communication between the components of the control system 300. For example, the CPU 305 may act as the master device for a communication bus between multiple components of the control system 300. As illustrated, in one embodiment, the CPU 305 communicates with the power module 318. For example, the CPU 305 may provide power distribution and/or conversion to the other components of the control system 300 and may also monitor battery power or battery life. In addition, the CPU 305 may function so as to temporarily suspend or decrease power to the control system 300 when a user is in a sitting or a standing position. Such control provides for energy conservation during periods of decreased use. The CPU 305 may also process error handling, such as when communication fails between components, an unrecognized signal or waveform is received from the sensor module 302, or when the feedback from the control drive module 310 or the ankle device 304 causes an error or appears corrupt.

In yet other embodiments of the invention, the CPU 305 uses or computes a security factor when analyzing information from the sensor module 302 and/or sending commands to the control drive module 310. For example, the security factor may include a range of values, wherein a higher value indicates a higher degree of certainty associated with a determined locomotion type of the user, and a lower security factor indicates a lower degree of certainty as to the locomotion type of the user. In one embodiment of the invention, adjustments are not made to the ankle device 304 unless the locomotion type of the user is recognized with a security factor above a predetermined threshold value.

In one embodiment, the CPU 305 includes modules that comprise logic embodied in hardware or firmware, or that comprise a collection of software instructions written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

FIG. 9 further depicts CPU 305 including a memory 306 for storing instructions and/or data. For example, the memory 306 may store one or more of the following types of data or instructions: an error log for the other components of the control system 300; information regarding gait patterns or curves; information regarding past activity of the user (e.g., number of steps); control parameters and set points; information regarding software debugging or upgrading; preprogrammed algorithms for basic movements of the prosthetic or orthotic system; calibration values and parameters relating to the sensor module 302 or other components; instructions downloaded from an external device; combinations of the same or the like.

The memory 306 may comprise any buffer, computing device, or system capable of storing computer instructions and/or data for access by another computing device or a computer processor. In one embodiment, the memory 306 is a cache that is part of the CPU 305. In other embodiments of the invention, the memory 306 is separate from the CPU 305. In other embodiments of the invention, the memory 306 comprises random access memory (RAM) or may comprise other integrated and accessible memory devices, such as, for example, read-only memory (ROM), programmable ROM (PROM), and electrically erasable programmable ROM (EEPROM). In another embodiment, the memory 306 comprises a removable memory, such as a memory card, a removable drive, or the like.

In one embodiment, the CPU 305 may also be configured to receive through the interface module 308 user- or activity-specific instructions from a user or from an external device. The CPU 305 may also receive updates to already existing instructions. Furthermore, the CPU 305 may communicate with a personal computer, a personal digital assistant, or the like so as to download or receive operating instructions. Activity-specific instructions may include, for example, data relating to cycling, driving, ascending or descending a ladder, adjustments from walking in snow or sand, or the like.

In one embodiment, the interface module 308 comprises an interface that the user accesses so as to control or manage portions or functions of the prosthetic or orthotic system. In one embodiment, the interface module 308 is a flexible keypad having multiple buttons and/or multiple light emitting diodes (LEDs) usable to receive information from and/or convey information to a user. For example, the LEDs may indicate the status of a battery or may convey a confirmation signal to a user. The interface module 308 may be advantageously located on the ankle device 304. Furthermore, the interface module 308 may comprise a USB connector usable for communication to an external computing device, such as a personal computer.

In a further embodiment, the interface module 308 comprises an on/off switch. In another embodiment, the interface module 308 may receive input regarding the user-controlled heel height or a forced relaxed mode of the prosthetic or orthotic system. In other embodiments, the user may adjust the type of response desired of the prosthesis or enable/disable particular functions of the ankle device 304. The input from the user may be entered directly via the interface module 308, such as through actuating a button, or user input may be received via a remote control.

The interface module 308 may comprise a touch screen, buttons, switches, a vibrator, an alarm, or other input-receiving or output structures or devices that allow a user to send instructions to or receive information from the control system 300. In another embodiment of the invention, the interface module 308 comprises an additional structure, such as a plug, for charging a battery powering the control system 300, such as at home or in a vehicle. In other embodiments of the invention, the interface module 308 may also communicate directly or indirectly with components of the control system 300 other than the CPU 305.

The control drive module 310 is used to translate high-level plans or instructions received from the CPU 305 into low-level control signals to be sent to the actuator 316. In one embodiment, the control drive module 310 comprises a printed circuit board that implements control algorithms and tasks related to the management of the actuator 316. In addition, the control drive module 310 may be used to implement a hardware abstraction layer that translates the decision processes of the CPU 305 to the actual hardware definition of the actuator 316. In another embodiment of the invention, the control drive module 310 may be used to provide feedback to the CPU 305 regarding the position or movement of the actuator 316 or ankle device 304. The control drive module 310 may also be used to adjust the actuator 316 to a new "neutral" setting upon detection by the CPU 305 that the user is traveling on an angled surface.

In one embodiment of the invention, the control drive module 310 is located within the ankle device 304. In other embodiments, the control drive module 310 may be located on the outside of the ankle device 304, such as on a socket, or remote to the ankle device 304.

The actuator 316 provides for the controlled movement of the ankle device 304. In one embodiment, the actuator 316 functions similarly to the actuator 116 described with respect to FIGS. 1-6, which actuator 116 controls the ankle motion of the prosthesis 100. In other embodiments of the invention, the actuator 316 may be configured to control the motion of an orthotic device, such as a brace or other type of support structure.

The ankle device 304 comprises any structural device that is used to mimic the motion of a joint, such as an ankle, and that is controlled, at least in part, by the actuator 316. In particular, the ankle device 304 may comprise a prosthetic device or an orthotic device.

The power module 318 includes one or more sources and/or connectors usable to power the control system 300. In one embodiment, the power module 318 is advantageously portable, and may include, for example, a rechargeable battery, as discussed previously. As illustrated in FIG. 9, the power module 318 communicates with the control drive module 310 and the CPU 305. In other embodiments, the power module 318 communicates with other control system 300 components instead of, or in combination with, the control drive module 310 and the CPU 305. For example, in one embodiment, the power module 318 communicates directly with the sensor module 302. Furthermore, the power module 318 may communicate with the interface module 308 such that a user is capable of directly controlling the power supplied to one or more components of the control system 300.

The components of the control system 300 may communicate with each other through various communication links. FIG. 9 depicts two types of links: primary communication links, which are depicted as solid lines between the components, and secondary communication links, which are depicted as dashed lines. In one embodiment, primary communication links operate on an established protocol. For example, the primary communication links may run between physical components of the control system 300. Secondary communication links, on the other hand, may operate on a different protocol or level than the primary communication links. For example, if a conflict exists between a primary communication link and a secondary communication link, the data from the primary communication link will override the data from the secondary communication link. The secondary communication links are shown in FIG. 9 as being communication channels between the control system 300 and the environment. In other embodiments of the invention, the modules may communicate with each other and/or the environment through other types of communication links or methods. For example, all communication links may operate with the same protocol or on the same level of hierarchy.

It is also contemplated that the components of the control system 300 may be integrated in different forms. For example, the components can be separated into several subcomponents or can be separated into more devices that reside at different locations and that communicate with each other, such as through a wired or wireless network. For example, in one embodiment, the modules may communicate through RS232 or serial peripheral interface (SPI) channels. Multiple components may also be combined into a single component. It is also contemplated that the components described herein may be integrated into a fewer number of modules. One module may also be separated into multiple modules.

Although disclosed with reference to particular embodiments, the control system 300 may include more or fewer components than described above. For example, the control system 300 may further include an actuator potentiometer usable to control, or fine-tune, the position of the actuator 316. The user may also use the actuator potentiometer to adjust the heel height of the ankle device 304. In one embodiment, the actuator potentiometer communicates with the CPU 305. In other embodiments, the control system 300 may include a vibrator, a DC jack, fuses, combinations of the same, or the like.

Examples of similar or other control systems and other related structures and methods are disclosed in U.S. patent application Ser. No. 10/463,495, filed Jun. 17, 2003, entitled "ACTUATED LEG PROSTHESIS FOR ABOVE-KNEE AMPUTEES," now published as U.S. Publication No. 2004/0111163; U.S. patent application Ser. No. 10/600,725, filed Jun. 20, 2003, entitled "CONTROL SYSTEM AND METHOD FOR CONTROLLING AN ACTUATED PROSTHESIS," now published as U.S. Publication No. 2004/0049290; U.S. patent application Ser. No. 10/627,503, filed Jul. 25, 2003, entitled "POSITIONING OF LOWER EXTREMITIES ARTIFICIAL PROPRIOCEPTORS," now published as U.S. Publication No. 2004/0088057; and U.S. patent application Ser. No. 10/721,764, filed Nov. 25, 2003, entitled "ACTUATED PROSTHESIS FOR AMPUTEES," now published as U.S. Publication No. 2004/0181289; each which is herein incorporated by reference in its entirety and is to be considered as part of this specification. In addition, other types of control systems that may be used in embodiments of the present invention are disclosed in U.S. Provisional Application No. 60/551,717, entitled "CONTROL SYSTEM FOR PROSTHETIC KNEE," filed Mar. 10, 2004; U.S. Provisional Application No. 60/569,511, entitled "CONTROL SYSTEM AND METHOD FOR A PROSTHETIC KNEE," filed May 7, 2004; and U.S. Provisional Application No. 60/572,996, entitled "CONTROL SYSTEM AND METHOD FOR A PROSTHETIC KNEE," filed May 19, 2004, which are herein incorporated by reference in their entireties to be considered as part as this specification.

FIG. 10 is a table that depicts possible control signals that may be involved in adjusting the ankle angle of a prosthetic or orthotic device when a user is transitioning between different states, or types of locomotion, according to one embodiment of the invention. In particular, the states listed in a column 402 identify a first state of the user, and the states listed in a row 404 identify a second state of the user, or the state to which the user is transitioning. The remainder of the table identifies possible actions that may be taken by the prosthetic or orthotic device with respect to the ankle angle. "User set point" is the neutral, or default, value that may be set during shoe heel height adjustment. The angles specified are examples of changes to the ankle angle of the prosthetic or orthotic device. For example, when a user is transitioning from a "stance" state to an "ascending stairs" state, the ankle angle may be adjusted to the angle of the stairs, such as for example, −10 degrees (or 10 degrees dorsiflexion). Ankle angles given in the "Incline (up)" and "Decline" columns reflect threshold levels of ankle angle adjustment depending on the angle of the incline.

The following table (TABLE 2) illustrates possible ankle motion strategies for one embodiment of the invention. The first column of TABLE 2 lists different types of locomotion types or gait patterns that may be frequently detected. The second column of TABLE 2 identifies examples of ankle angle adjustment of the prosthetic or orthotic device during the swing phase of each of the identified locomotion types.

TABLE 2

| Locomotion Type/Gait Pattern | Ankle Motion During Swing Phase of Ankle Device |
|---|---|
| Level Ground Walking | Toe clearance during swing |
| Ascending Stairs | Anide adjusts to dorsiflexion (e.g., 7.5°) |
| Descending Stairs | Ankle adjusts to dorsiflexion (e.g., 5°) |
| Incline (up) | Ankle adjust to dorsiflexion:<br>a) Two incline angle threshold levels (x°, y°)<br>b) Stepwise (2 steps) angle adjustment (z°, w°)<br>  - Example: If incline angle > x°, ankle will adjust to −z°; if incline angle > y°, ankle will adjust to −w°, wherein x = 2.5° and y = 5°. |
| Decline | Ankle adjusts to plantarflexion:<br>a) Two decline angle threshold levels (x°, y°)<br>b) Stepwise (2 steps) angle adjustment (z°, w°)<br>  - Example: If decline angle > x°, ankle will adjust to z°; if decline angle > y°, ankle will adjust to w°, wherein x = 2.50 and y = 5° |
| Sitting/Relaxed | Set Heel Height |
| Adjust Heel Height | Stepless heel height adjustment up to 20° plantarflexion |

Figure 11:
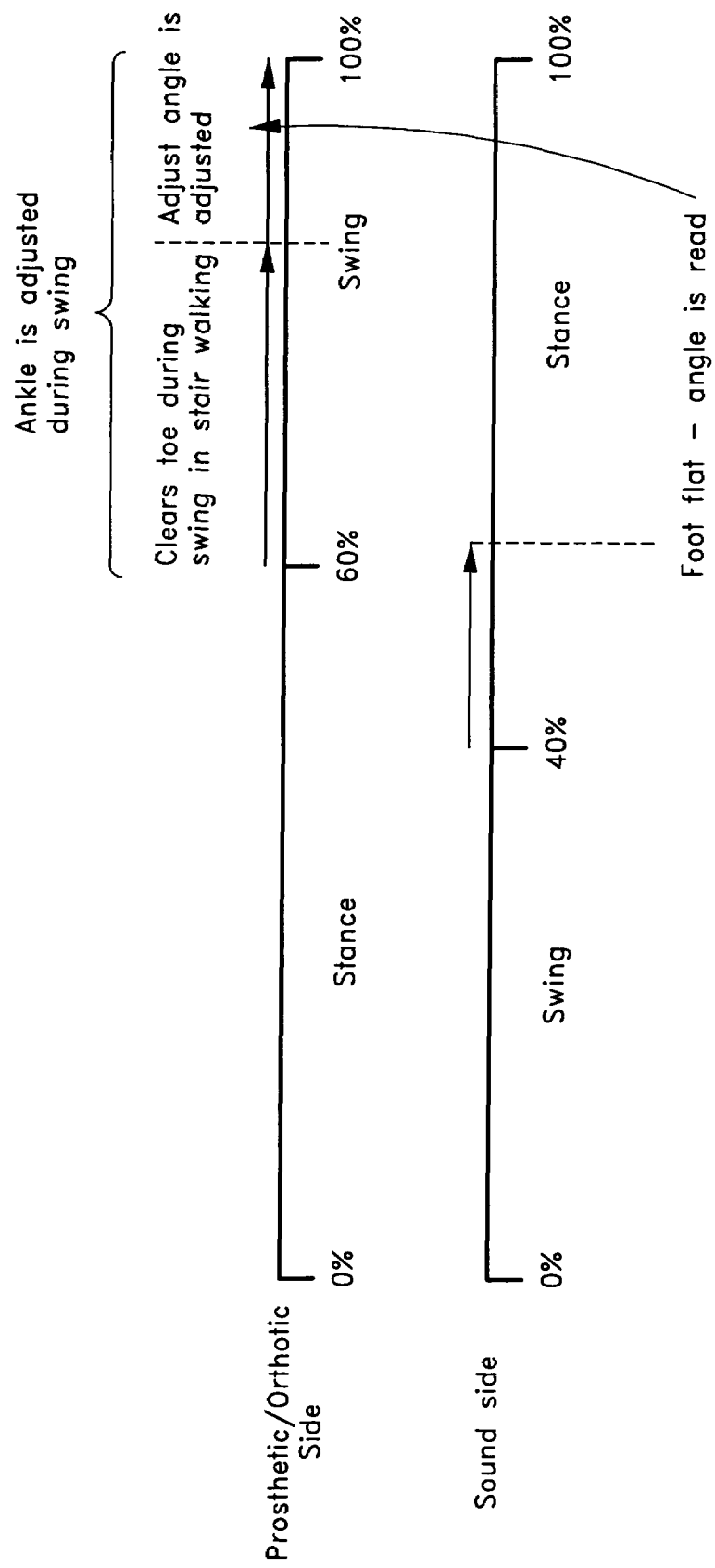
FIG. 11 is a graph depicting an exemplifying embodiment of the relationship between the control of a prosthetic or orthotic system and the motion of a corresponding sound limb.

FIG. 11 depicts a graph that illustrates the interaction and relationship between the control of a prosthetic or orthotic leg and the measurements taken from a healthy, sound leg. In particular, FIG. 11 depicts the movement of a prosthetic or orthotic leg and a healthy leg during one full stride of a user. For example, during approximately the first 60% of the stride, the graph shows the prosthetic or orthotic leg as being in a "stance" position or being planted on a surface, such as the ground. In one embodiment, during the beginning portion of the stance phase the ankle angle of the prosthetic or orthotic leg may decrease (dorsiflexion). Toward the end of the stance phase the ankle angle of the prosthetic or orthotic leg may then increase (plantarflexion) to facilitate natural stride movements. In other embodiments of the invention, the ankle angle of the prosthetic or orthotic leg is not actively adjusted during the stance phase. During a portion of this same period, up to approximately point 40%, the healthy leg may be in a swinging position, wherein the healthy leg is not in contact with the ground. Between the points of approximately 40% and 60%, both legs are in contact with the ground.

From approximately point 60% to 100% (the end of the stride), the prosthetic or orthotic leg is in a swinging position, and the healthy leg is in contact with the ground. The graph in FIG. 11 shows that the ankle angle of the prosthetic or orthotic leg is adjusted during the swing phase. This angle adjustment may be based on previous measurements of the healthy leg during the swing phase of the healthy leg. In one embodiment, during the beginning portion of the swing phase of the prosthetic or orthotic leg, the ankle angle of the prosthetic or orthotic leg may decrease. This allows, for example, a toe portion of the prosthetic or orthotic leg to clear stairs. Toward the latter portion of the swing phase of the prosthetic or orthotic leg, the ankle angle of the prosthetic or orthotic leg may then increase before contacting the ground. In other embodiments, the angle adjustment is based on readings taken by sensors on the prosthetic side.

It is to be understood that FIG. 11 is illustrative of the functioning of one embodiment of the invention under certain conditions. Other embodiments or circumstances may require a longer or shorter stance or swing phase and require other adjustments to the angle of the ankle portion of the prosthetic leg.

While certain embodiments of the inventions have been described, these embodiments have been presented by way of example only, and are not intended to limit the scope of the inventions. Indeed, the novel methods and systems described herein may be embodied in a variety of other forms. For example, the foregoing may be applied to the motion-control of joints other than the ankle, such as a knee or a shoulder. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method for controlling an ankle device associated with the movement of a limb, the method comprising:
   monitoring, with at least one sensor, at least one of position and movement of an ankle device associated with a limb throughout at least one gait cycle, wherein the device comprises a foot unit, a lower limb member, and at least one actuator;
   generating data indicative of the at least one of position and movement throughout the at least one gait cycle;
   processing the data with a processing module to determine if the data corresponds to one of a plurality of defined gait patterns or events, wherein information defining said plurality of gait patterns or events is stored in a memory of the device;
   determining ankle-angle adjustments corresponding to a determined gait pattern or event; and
   adjusting the device based on the determined ankle-angle adjustments corresponding to the determined gait pattern or event, wherein the adjusting comprises actuating the at least one actuator to move the lower limb member relative to the foot unit in a manner substantially mimicking movement of a healthy ankle, said ankle-angle adjustments being applied over a swing phase of subsequent gait cycles until a state transition is detected from the determined gait pattern or event to a different gait pattern or event.

2. The method of claim 1, wherein the device comprises an orthotic device.

3. The method of claim 1, wherein the device comprises a prosthetic device.

4. The method of claim 1, additionally comprising determining a security factor, wherein the actuating occurs only if the security factor exceeds a determined threshold.

5. The method of claim 1, additionally comprising substantially locking the device in a fixed position when a battery power level drops below a determined threshold.

6. The method of claim 1, wherein the at least one sensor is located on the device.

7. The method of claim 1, wherein the actuating comprises at least one of the following: extending and contracting the at least one actuator.

8. The method of claim 1, additionally comprising adjusting a heel height of the device.

9. The method of claim 1, wherein the at least one sensor is located on the limb.

10. A method for controlling a prosthetic ankle device, the method comprising:
monitoring, with at least one sensor, at least one of position and movement of a prosthetic ankle device, wherein the at least one sensor generates data indicative of the at least one of position and movement of the prosthetic ankle device, and wherein the prosthetic ankle device comprises a foot unit, a lower limb member, and at least one actuator;
receiving and processing the data with a control module to determine if the data corresponds to one of a plurality of defined gait patterns or events, wherein information defining the plurality of gait patterns or events is stored in a memory of the device;
outputting with the control module at least one control signal based on a determined gait pattern or event; and
adjusting the prosthetic ankle device based at least upon the control signal, wherein said adjusting comprises actuating the at least one actuator to move the lower limb member relative to the foot unit in a manner substantially mimicking movement of a healthy ankle, said actuating occurring as the prosthetic ankle device is operated during a swing phase of the device, and wherein said actuating does not occur during a stance phase of the ankle device, and said adjusting being applied at least until a new gait pattern or event is determined.

11. The method of claim 10, additionally comprising receiving and processing data indicative of at least one terrain variable.

12. The method of claim 10, wherein the adjusting comprises movement of the prosthetic ankle device within the range of approximately ten degrees dorsiflexion to approximately twenty degrees plantarflexion.

13. The method of claim 10, wherein the at least one sensor is positioned on the prosthetic ankle device.

14. The method of claim 13, wherein the at least one sensor comprises at least one accelerometer.

15. The method of claim 10, wherein the monitoring comprises monitoring acceleration of the prosthetic ankle device in multiple different axes.

16. The method of claim 10, additionally comprising providing dampening to counteract unwanted movements of the prosthetic ankle device.

17. The method of claim 10, additionally comprising substantially locking the prosthetic ankle device at a fixed angle when a power source associated with the prosthetic ankle device falls below a particular threshold power level.

18. The method of claim 10, additionally comprising receiving from a user a second signal indicative of a heel height adjustment.

19. The method of claim 10, wherein adjusting the prosthetic ankle device comprises causing rotation about a pivot point of the prosthetic ankle device.

20. The method of claim 11, wherein the at least one terrain variable includes data indicative of a slope of the ground surface.

21. The method of claim 1, wherein the device associated with a limb is a device attachable to a limb.

22. The method of claim 1, wherein the plurality of defined gait patterns or events comprises at least one of the following: stance, level ground walking, ascending stairs, descending stairs, incline, decline, sitting down, sitting, standing up, adjust heel height, off, heel height calibration, sensor calibration, neutral, relax, and pants.

23. A method for controlling a prosthetic ankle device, the method comprising:
monitoring, with at least one sensor, at least one of position and movement of a prosthetic ankle device, wherein the device comprises a foot unit, a single lower limb member pivotally attached to the foot unit and at least one actuator having a first end connected to the foot unit and a second end connected to the lower limb member, the at least one actuator configured to adjust an ankle angle between the foot unit and the lower limb member;
generating data indicative of the at least one of position and movement;
processing the data with a processing module to determine a gait cycle phase;
during stance phases, not adjusting the ankle angle of the device; and
during swing phase, actuating the at least one actuator to move the foot unit relative to the lower limb member in a manner that substantially mimics movement of a healthy ankle by first decreasing an ankle angle of the device to a dorsiflexion position and then increasing the ankle angle of the device to a plantarflexion position.

24. The method of claim 23, wherein the device comprises a single actuator.

25. The method of claim 23, wherein the at least one actuator is configured to adjust the angle between the foot unit and the lower limb member in only a substantially vertical plane.

26. The method of claim 1, comprising using the data to generate a waveform that portrays the gait of the limb.

27. The method of claim 1, further comprising sampling data over at least one stride before determining if the data corresponds to one of a plurality of gait patterns or events.

28. The method of claim 10, wherein the plurality of defined gait patterns or events comprises at least one of the following: standing, level ground walking, ascending stairs, descending stairs, walking up an incline, walking down a decline, sitting down, sitting, standing up, adjusting heel height, neutral, relaxing, and putting on pants.

29. The method of claim 10, wherein the data is generated according to an adjustable sampling rate.

30. The method of claim 29, wherein the sampling rate is 100 hertz (Hz) or more.

31. The method of claim 1, wherein said ankle-angle adjustments being applied over a swing phase of subsequent gait cycles until the state transition is detected comprises repeatedly actuating the at least one actuator during swing phases of subsequent gait cycles until the state transition is detected, said ankle-angle adjustments during swing phases comprising first decreasing an ankle angle of the device to a dorsiflexion position and then increasing the ankle angle of the device to a plantarflexion position before contacting ground.

32. The method of claim 1, wherein said ankle-angle adjustments being applied over a swing phase of subsequent gait cycles until the state transition is detected comprises actuating the at least one actuator during swing phases of subsequent gait cycles until the state transition is detected, wherein ankle-angle adjustments are not applied during stance phases of subsequent gait cycles.

33. The method of claim 1, wherein a gait cycle comprises one full stride of a user.

34. The method of claim 1, wherein the determined ankle-angle adjustments comprise at least one of the following: toe clearance; user set point; set heel height; relax ankle; a desired degree of dorsiflexion; a desired degree of plantarflexion; ten degrees of dorsiflexion; five degrees of dorsiflexion; seven and a half degrees of dorsiflexion; 20 degrees of plantarflexion; an ankle angle associated with an incline angle threshold level; an ankle angle associated with a decline angle threshold level; an ankle angle associated with an incline angle of five degrees; an ankle angle with an incline angle of two and a half degrees; an ankle angle associated with a decline angle of five degrees; and an ankle angle associated with a decline angle of two and a half degrees.

35. The method of claim 10, wherein said adjusting being applied at least until a new gait pattern or event is determined comprises actuating the at least one actuator, during a swing phase, to create an ankle angle between the lower limb member and the foot unit, wherein the ankle angle is not adjusted during stance phases of subsequent strides.

36. The method of claim 10, wherein said adjusting being applied at least until a new gait pattern or event is determined includes repeatedly actuating the at least one actuator during swing phases of subsequent strides until a state transition is detected to the new gait pattern or event, said actuating comprising first decreasing an ankle angle of the device to a dorsiflexion position and then increasing the ankle angle of the device to a plantarflexion position before contacting ground.

37. The method of claim 23, wherein a gait cycle comprises one full stride of a user.

38. The method of claim 23, wherein not adjusting the ankle angle of the device comprises locking the device into a neutral position.

39. The method of claim 23, wherein the dorsiflexion position is at least 5 degrees from a neutral position, and wherein the ankle angle of the device in the dorsiflexion position is less than the ankle angle of the device in the neutral position.

40. The method of claim 23, wherein the plantarflexion position is up to twenty degrees from a neutral position, and wherein the ankle angle of the device in the plantarflexion position is greater than the ankle angle of the device in the neutral position.

41. The method of claim 23, wherein, during the swing phase, the ankle angle of the device is first adjusted from a neutral position to the dorsiflexion position, is then adjusted from the dorsiflexion position to the plantarflexion position, and is then adjusted from the plantarflexion position back to the neutral position.

42. The method of claim 23, wherein the stance phase is approximately sixty percent of a stride of a user of the device.

43. The method of claim 23, wherein the swing phase is approximately forty percent of a stride of a user of the device.

* * * * *

UNITED STATES PATENT AND TRADEMARK OFFICE
CERTIFICATE OF CORRECTION

PATENT NO. : 7,431,737 B2 Page 1 of 1
APPLICATION NO. : 11/057391
DATED : October 7, 2008
INVENTOR(S) : Heidrun G. Ragnarsdottir et al.

It is certified that error appears in the above-identified patent and that said Letters Patent is hereby corrected as shown below:

Title page 3, column 1, line 44, Delete "11/2001" and insert -- 11/2000 --, therefor.

At column 10, lines 26-27, Delete "plantarfiexion" and insert -- plantarflexion --, therefor.

At column 19, line 27, Delete "Anide" and insert -- Ankle --, therefor.

At column 19, line 34, Delete "plantarfiexion" and insert -- plantarflexion --, therefor.

At column 19, line 37, Delete "2.50" and insert -- 2.5° --, therefor.

At column 21, line 43, Delete "plantarfiexion" and insert -- plantarflexion --, therefor.

At column 22, line 30, Delete "plantarfiexion" and insert -- plantarflexion --, therefor.

At column 22, line 61, Delete "plantarfiexion" and insert -- plantarflexion --, therefor.

At column 23, line 8, Delete "plantarfiexion" and insert -- plantarflexion --, therefor.

At column 23, lines 10-11, Delete "plantarfiexion" and insert -- plantarflexion --, therefor.

At column 24, line 2, Delete "plantarfiexion" and insert -- plantarflexion --, therefor.

At column 24, line 13, Delete "plantarfiexion" and insert -- plantarflexion --, therefor.

At column 24, line 15, Delete "plantarfiexion" and insert -- plantarflexion --, therefor.

At column 24, line 21, Delete "plantarfiexion" and insert -- plantarflexion --, therefor.

At column 24, line 22, Delete "plantarfiexion" and insert -- plantarflexion --, therefor.

Signed and Sealed this

Sixth Day of July, 2010

David J. Kappos
*Director of the United States Patent and Trademark Office*

(12) EX PARTE REEXAMINATION CERTIFICATE (9974th)
United States Patent
Ragnarsdottir et al.

(10) Number: US 7,431,737 C1
(45) Certificate Issued: Dec. 9, 2013

(54) SYSTEM AND METHOD FOR MOTION-CONTROLLED FOOT UNIT

(75) Inventors: Heidrun G. Ragnarsdottir, Reykjavik (IS); Arinbjorn V. Clausen, Reykjavik (IS); Hjordis Thorhallsdottir, Reykjavik (IS); Helgi Jonsson, Reykjavik (IS)

(73) Assignee: Ossur HF., Reykjavik (IS)

Reexamination Request:
No. 90/012,731, Dec. 5, 2012

Reexamination Certificate for:
Patent No.: 7,431,737
Issued: Oct. 7, 2008
Appl. No.: 11/057,391
Filed: Feb. 11, 2005

Certificate of Correction issued Jul. 6, 2010

Related U.S. Application Data

(60) Provisional application No. 60/544,259, filed on Feb. 12, 2004, provisional application No. 60/588,232, filed on Jul. 15, 2004.

(51) Int. Cl.
*A61F 2/24* (2006.01)
*A61F 2/66* (2006.01)

(52) U.S. Cl.
USPC .................................. 623/24; 623/47; 623/50

(58) Field of Classification Search
None
See application file for complete search history.

(56) References Cited

To view the complete listing of prior art documents cited during the proceeding for Reexamination Control Number 90/012,731, please refer to the USPTO's public Patent Application Information Retrieval (PAIR) system under the Display References tab.

*Primary Examiner* — David O. Reip

(57) ABSTRACT

A system and method associated with the movement of a limb. In one example, the system, such as a prosthetic or orthotic system, includes an actuator that actively controls, or adjusts, the angle between a foot unit and a lower limb member. A processing module may control movement of the actuator based on data obtained from a sensor module. For instance, sensing module data may include information relating to the gait of a user and may be used to adjust the foot unit to substantially mimic the movement of a natural, healthy ankle. The system may further accommodate, for example, level ground walking, traveling up/down stairs, traveling up/down sloped surfaces, and various other user movements. In addition, the processing module may receive user input or display output signals through an external interface. For example, the processing module may receive a heel height input from the user.

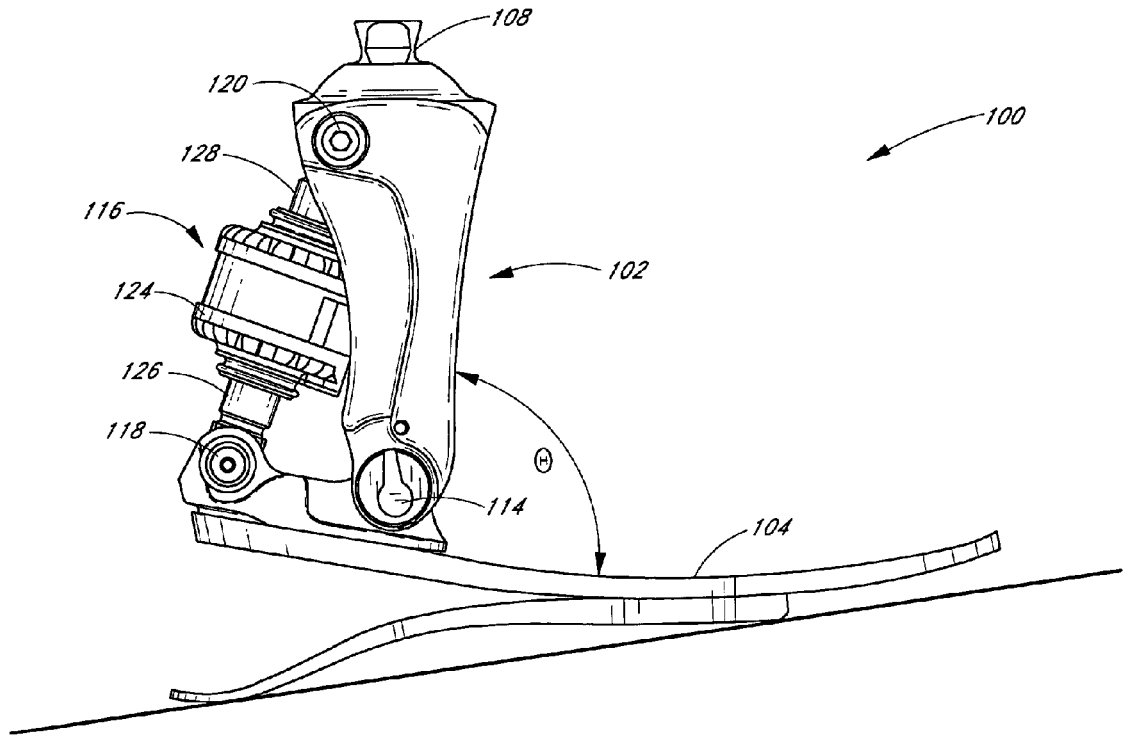

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-43 is confirmed.

\* \* \* \* \*